United States Patent
Zhang et al.

(10) Patent No.: US 11,213,614 B2
(45) Date of Patent: Jan. 4, 2022

(54) VASCULARIZED BIPHASIC TISSUE CONSTRUCTS

(71) Applicant: The George Washington University, Washington, DC (US)

(72) Inventors: Lijie G. Zhang, Arlington, VA (US); Haitao Cui, Arlington, VA (US); Wei Zhu, Washington, DC (US)

(73) Assignee: The George Washington University, Washington, DC (US)

( * ) Notice: Subject to any disclaimer, the term of this patent is extended or adjusted under 35 U.S.C. 154(b) by 0 days.

(21) Appl. No.: 15/926,679

(22) Filed: Mar. 20, 2018

(65) Prior Publication Data
US 2019/0030212 A1    Jan. 31, 2019

Related U.S. Application Data

(60) Provisional application No. 62/473,830, filed on Mar. 20, 2017.

(51) Int. Cl.
*A61L 27/54* (2006.01)
*A61L 27/52* (2006.01)
(Continued)

(52) U.S. Cl.
CPC .............. *A61L 27/54* (2013.01); *A61F 2/28* (2013.01); *A61F 2/3094* (2013.01);
(Continued)

(58) Field of Classification Search
None
See application file for complete search history.

(56) References Cited

U.S. PATENT DOCUMENTS

| 2002/0119177 A1* | 8/2002 | Bowman | A61L 27/56 424/423 |
| 2008/0149566 A1* | 6/2008 | Messersmith | C09D 5/1681 210/702 |

(Continued)

FOREIGN PATENT DOCUMENTS

WO    WO-2010044758 A1 *    4/2010    ............... A61F 2/28

OTHER PUBLICATIONS

Bae, et al, "Discontinuous Release of Bone Morphogenetic Protein-2 Loaded Within Interconnected Pores of Honeycombe-Like Polycaprolactone Scaffold Promotes Bone Healing in Large Bone Defects of Rabit Ulna", Tissue Engineering: Part A, vol. 17, No. 19-20, 2011, pp. 2389-2397 (Year: 2011).*

(Continued)

*Primary Examiner* — Leslie Lopez
(74) *Attorney, Agent, or Firm* — Kory D. Christensen

(57) ABSTRACT

Biphasic tissue constructs that include a scaffold having one or more channels, a vascular portion comprising a hydrogel at least partially disposed in the one or more channels, and a first bioactive growth factor and a second bioactive growth factor different from the first bioactive growth factor, the first bioactive growth factor localized to the scaffold and the second bioactive growth factor localized to the vascular portion. The first bioactive growth factor may be bone morphogenetic protein 2 (BMP2) peptide and the second bioactive growth factor may be vascular endothelial growth factor (VEGF) peptide.

17 Claims, 20 Drawing Sheets

(51) Int. Cl.
| | |
|---|---|
| A61K 35/51 | (2015.01) |
| A61K 35/28 | (2015.01) |
| A61K 38/18 | (2006.01) |
| A61F 2/28 | (2006.01) |
| A61F 2/30 | (2006.01) |
| A61L 27/26 | (2006.01) |
| A61L 27/18 | (2006.01) |
| A61L 27/34 | (2006.01) |
| A61L 27/38 | (2006.01) |
| B33Y 10/00 | (2015.01) |
| B33Y 70/00 | (2020.01) |
| B33Y 80/00 | (2015.01) |

(52) U.S. Cl.
CPC .......... *A61F 2/30771* (2013.01); *A61K 35/28* (2013.01); *A61K 35/51* (2013.01); *A61K 38/1866* (2013.01); *A61K 38/1875* (2013.01); *A61L 27/18* (2013.01); *A61L 27/26* (2013.01); *A61L 27/34* (2013.01); *A61L 27/3808* (2013.01); *A61L 27/3834* (2013.01); *A61L 27/3886* (2013.01); *A61L 27/52* (2013.01); *B33Y 10/00* (2014.12); *B33Y 70/00* (2014.12); *B33Y 80/00* (2014.12); *A61F 2002/2817* (2013.01); *A61F 2002/30014* (2013.01); *A61F 2002/30062* (2013.01); *A61F 2002/3092* (2013.01); *A61F 2002/30327* (2013.01); *A61F 2002/30677* (2013.01); *A61F 2002/30784* (2013.01); *A61F 2002/30985* (2013.01); *A61F 2310/0097* (2013.01); *A61F 2310/00976* (2013.01); *A61L 2300/414* (2013.01); *A61L 2430/02* (2013.01); *A61L 2430/40* (2013.01)

(56) References Cited

U.S. PATENT DOCUMENTS

| | | | | |
|---|---|---|---|---|
| 2012/0171257 | A1* | 7/2012 | Inane | A61L 27/18 424/400 |
| 2016/0067375 | A1 | 3/2016 | Holmes et al. | |
| 2016/0287756 | A1* | 10/2016 | Lewis | B29C 64/40 |
| 2017/0281827 | A1* | 10/2017 | Baker | A61L 27/30 |
| 2018/0015207 | A1 | 1/2018 | Cui et al. | |

OTHER PUBLICATIONS

Aubin, etal, "Directed 3D Cell Alignment and Elongation in Microengineered Hydrogels", Biomaterials, vol. 31, 2010, pp. 6941-6951 (Year: 2010).*

Nguyen, et al, "Vascularized Bone Tissue Engineering: Approaches for Potential Improvement", Tissue Engineering: Part B, vol. 18, No. 5, 2012, pp. 363-282 (Year: 2012).*

Baldwin et al., "In Vitro Pre-Vascularisation of Tissue-Engineered Constructs A Co-Culture Perspective," Vascular Cell, 2014, 6:13, pp. 1-16.

Billiet et al., "A Review of Trends and Limitations in Hyrogel-Rapid Prototyping for Tissue Engineering," Biomaterials 33 (2012) pp. 6020-6041.

Blache et al., "Dual Role of Mesenchymal Stem Cells Allowed for Microvascularized Bone Tissue-Like Environments in PEG Hydrogels," Advanced Healthcare Materials, 2016, 5, pp. 489-498.

Bose et al., "Bone Tissue Engineering Using 3D Printing," Materials Today, vol. 16, No. 12, Dec. 2013, pp. 496-504.

Brazamara et al., "Blood Flow and Enothelial Cell Phenotype Regulation During Sprouting Angiogenesis," Med Biol Eng Comput (2016) 54:547-558.

Chen et al., "Functional Human Vascular Network Generated in Photocrosslinkable Gelatin Methacrylate Hydrogels," Advanced Functional Materials, 2012, 22, pp. 2027-2039.

Cui et al., "Combined Angiogenic and Osteogenic Factor Delivery for Bone Regenerative Engineering," Current Pharmaceutical Design, 2013, 19, pp. 3374-3383.

Derby, "Printing and Prototyping of Tissues and Scaffolds," Science, vol. 338, Nov. 16, 2012, pp. 921-926.

Do et al., "3D Printing of Scaffolds for Tissue Regeneration Applications," Advanced Healthcare Materials, 2015, 4, pp. 1742-1762.

Galie et al., "Fluid Shear Stress Threshold Regulates Angiogenic Sprouting," PNAS, Jun. 3, 2014, vol. 111, No. 22, pp. 7968-7973.

Griffith et al., "Tissue Engineering—Current Challenges and Expanding Opportunities," Science, vol. 295, Feb. 8, 2002, pp. 1009-1014.

Kanczler et al., "Osteogenesis and Angiogenesis: The Potential for Engineering Bone," European Cells and Materials, vol. 15, 2008, pp. 100-114.

Kang et al., "Engineering Vascularized Bone Grafts by Integrating a Biomimetic Periosteum and βTCP Scaffold," AC Appl. Interfaces, 2014, 6, pp. 9622-9633.

Koshy et al., "Injectable, Porous, and Cell-Responsive Gelatin Cryogels," Biomaterials 35 (2014) pp. 2477-2487.

Lee et al., "A Novel Flow Bioreactor for In Vitro Microvascularization," Tissue Engineering: Part C, vol. 16, No. 5, 2010, pp. 1191-1200.

Marga et al., "Toward Engineering Functional Organ Modules by Additive Manufacturing," Biofabrication 4 (2012), pp. 1-12.

Melchels et al., "Additive Manufacturing of Tissues and Organs," Progress in Polymer Science 37 (2012) pp. 1079-1104.

Mitchell et al., "Engineering Growth Factors for Regenerative Medicine Applications," Acta Biomaterialia 30 (2016) pp. 1-12.

Miyazono et al., "Bone Morphogenetic Protein Receptors and Signal Transduction," J. Biochem, 2010;147(1):35-51.

Murphy et et al., 3D Bioprinting of Tissues and Organs, Nature Biotechnology, vol. 32, No. 8, Aug. 2014, pp. 773-785.

Nguyen et al., "Vascularized Bone Tissue Engineering: Approaches for Potential Improvement," Tissue Engineering: Part B, vol. 8, No. 5, 2012, pp. 363-382.

Obrien et al., "Three-Dimensional Printing of Nanomaterials Scaffolds for Complex Tissue Regeneration," Tissue Engineering: Part B, vol. 21, No. 1, 2015, pp. 103-114.

Oryan et al., "Bone Regenerative Medicine: Classic Options, Novel Strategies, and Future Directions," Journal of Orthopaedic Surgery and Research, 2014, 9:18, pp. 1-27.

Pagan et al., "Vascularization in Bone Tissue Engineering Constructs," Annals of Biomedical Engineering, vol. 43, No. 3, Mar. 2015, pp. 718-729.

Perez et al., "Naturally and Synthetic Smart Composite Biomaterials for Tissue Regeneration," Advanced Drug Delivery Reviews, 65 (2013) 471-496.

Place et al., "Complexity in Biomaterials for Tissue Engineering," Nature Materials, vol. 8, Jun. 2009, pp. 457-470.

Roux et al., "Engineering Clinically Relevant Volumes of Vascularized Bone," J. Cell. Mol. Med. vol. 19, No. 5 ,2015, pp. 903-914.

Shah et al., "Adaptive Growth Factor Delivery from a Polyelectrolyte Coating Promotes Synergistic Bone Tissue Repair and Reconstruction," PNAS, Sep. 2, 2014, vol. 111, No. 35, pp. 12847-12852.

Skardal et al., "Biomaterials for Integration with 3-D Bioprinting," Annals of Biomedical Engineering, vol. 43, No. 3, Mar. 2015, pp. 730-746.

Tsigkou et al., "Engineered Vascularized Bone Grafts," PNAS, Sep. 11, 2018, vol. 115, No. 37, pp. 3311-3316.

Wang et al., Evaluating 3D-Printed Biomaterials as Scaffolds for Vascularized Bone Tissue Engineering, Advanced Materials, 2015, 27, pp. 138-144.

Wang et al., "Phage Nanofibers Induce Vascularized Osteogenesis in 3D Printed Bone Scaffolds," Advanced Materials, 2014, 26, pp. 4961-4966.

Webber et al., "Supramolecular Nanostructures that Mimic VEGF as a Strategy for Ischemic Tissue Repair," PNAS, Aug. 16, 2011, vol. 108, No. 33, pp. 13438-13443.

Wegst et al., "Bioinspired Structural Materials," Nature Materials, vol. 14, Jan. 2015, pp. 23-36.

Wragg et al., Shear Stress Regulated Gene Expressed and Angiogenesis in Vascular Endothelium, Microcirculation, 21: 290-300, 2014.

(56) References Cited

OTHER PUBLICATIONS

Zorlutuna et al., "Microfabricated Biomaterials for Engineering 3D Tissues," Advanced Materials, 2012, vol. 24, pp. 1782-1804.

* cited by examiner

BMP2 Peptide Sequences

VEGF Peptide Sequences

VASCULARIZED BIPHASIC TISSUE CONSTRUCTS

CROSS REFERENCE TO RELATED APPLICATIONS

This application claims priority from U.S. Provisional Application No. 62/473,830, entitled "An Integrated Approach for Fabricating Complicated Vascularized Constructs via Combining Multiple 3D Printing Platform Technique and Regional Bioactive Factors Immobilization Strategy," filed on Mar. 20, 2017, which is incorporated by reference in its entirety, for all purposes, herein.

STATEMENT OF GOVERNMENT SUPPORT

This invention was made with government support under grant no. DP2EB020549 awarded by the National Institute of Health. The government has certain rights in the invention.

FIELD

The present disclosure relates to three-dimensional bioprinted tissues. In particular, the present disclosure relates to vascularized tissue constructs and methods of fabricating vascularized tissue constructs using three-dimensional bioprinting techniques.

BACKGROUND

During the past three decades, tissue engineering has made great progress in fabricating various artificial tissues with simple structures, achieving partially functional restoration in fundamental research and in clinical applications. However, the vast majority of tissue types possess hierarchical, complicated characteristics both in structure and function. Despite continuous efforts to understand the complex biological mechanisms of the regeneration process in order to provide new knowledge for engineering the restoration of functional tissue, the effective recapitulation of the intrinsic complexity of native tissues has remained elusive.

In particular, native bone is a highly complex tissue with an intricate hierarchical architecture. Bone consists of mineral matrix, with entrapped bone cells, encircled by and interwoven with vascular networks. The blood vessels within native bone are crucial for transporting oxygen and nutrients to maintain skeletal tissue functions. In numerous traditional tissue engineering techniques, the spreading of different cells onto prefabricated scaffolds usually results in a random cellular distribution in 3D space thereby failing to replicate the complex hierarchical organization of functional tissue.

Three-dimensional (3D) bioprinting techniques may be used to precisely control the location of biomaterials and cells, making it an interesting investigational technique that may eventually offer comprehensive capacity for fabricating complicated macro and micro structures. Many attempts at bioprinting complex, biofunctional scaffolds have been made using ink-jet bioprinting, fused deposition modeling (FDM), selective laser sintering (SLS), and stereolithography (SLA), among others, independently. However, attempts to produce a biomimetic vascularized bone equivalent that possesses hierarchical and constituent complexities similar to native bone, have been unsuccessful. One obstacle to the use of 3D bioprinting to produce such constructs has been that monotypic model bioprinting, and its corresponding printing materials, have achieved limited success in the fabrication of complicated tissue structures with different intrinsic characteristics. Additional limitations include challenges with replicating suitable mechanical loading at different locations and facilitating regional differentiation induction. Accordingly, additional methods of fabricating vascularized tissue constructs, and particularly vascularized bone constructs, having one or more advantageous characteristics, using 3D bioprinting techniques are desirable.

BRIEF DESCRIPTION OF THE DRAWINGS

In order to describe the manner in which the advantages and features of the disclosure can be obtained, reference is made to embodiments thereof which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which.

DETAILED DESCRIPTION

Figure 1:
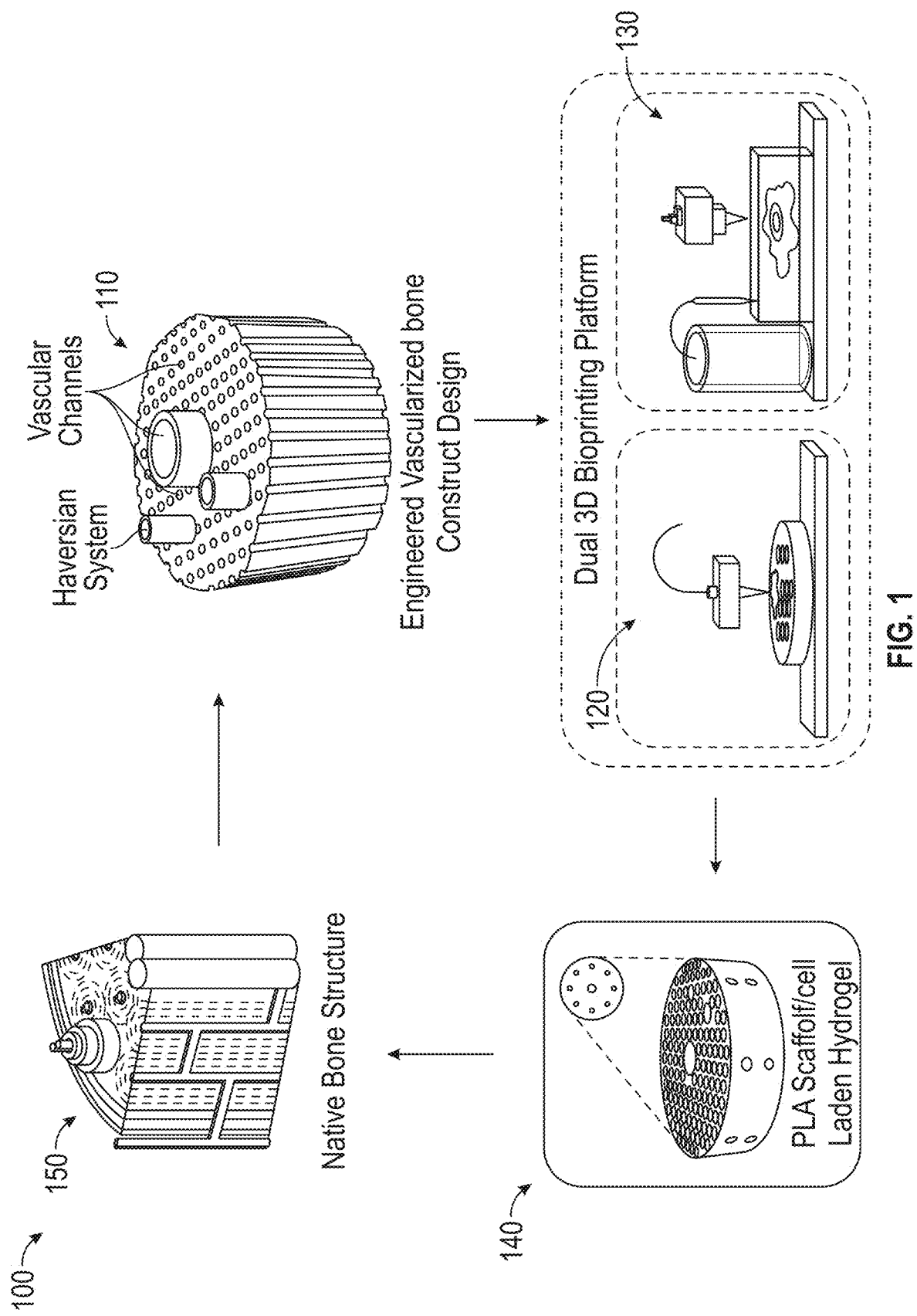
FIG. 1 is a schematic view of a biomimetic architectural design and hierarchical fabrication process of preparing engineered vascularized bone biophasic constructs using a dual 3D bioprinting platform, in accordance with certain exemplary embodiments of the present disclosure.

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure.

It should be understood at the outset that although illustrative implementations of one or more embodiments are illustrated below, the disclosed compositions and methods may be implemented using any number of techniques. The disclosure should in no way be limited to the illustrative implementations, drawings, and techniques illustrated herein, but may be modified within the scope of the appended claims along with their full scope of equivalents.

In the following discussion and in the claims, the terms "including" and "comprising" are used in an open-ended fashion, and thus should be interpreted to mean "including, but not limited to . . . ". As used herein, the terms "bioactive growth factor," "bioactive factor," and "growth factor," in all their forms, refers to a compound that influences cellular or physiological activities of animals or humans in vivo or in vitro. The compound may be, for example, a chemical, peptide, or protein. In at least some instances, a "bioactive growth factor," "bioactive factor, or "growth factor," may, for example, improve cell adhesion, proliferation, and differentiation, and/or other functions in tissue regeneration.

The various characteristics described in more detail below, will be readily apparent to those skilled in the art with the aid of this disclosure upon reading the following detailed description, and by referring to the accompanying drawings.

The present disclosure is directed to methods for preparing complex tissue constructs, including vascularized biphasic tissue constructs, which may include the combination of multiple 3D bioprinting platforms with regional immobilization strategies of bioactive factors. The presently disclosed methods can be employed to exert spatial control over construct microstructures, cell organization, mechanical loading and bioactive factor arrangement. The tissue constructs prepared according to the presently disclosed methods include regional bioactive factors integrated into biomimetic hierarchical architectures providing an innovative method and construct for multicellular tissue regeneration. In this study, we presented a novel dual 3D bioprinting approach in conjunction with regional bioactive peptide immobilization to fabricate vascularized tissue constructs. The present disclosure provides methods for obtaining a hierarchically biomimetic construct with multi-phasic characteristics that are suitable for complicated tissue regeneration, thereby resolving the current challenges and complexities associated with vascularized tissue.

In particular, the present application discloses complex vascularized biphasic tissue constructs that include a hard structure surrounded by a soft organic matrix that more closely mimics natural bone. The presently disclosed constructs may be fabricated on a dual 3D bioprinting platform comprised of a FDM 3D bioprinter and a SLA 3D bioprinter. In at least some instances, the methods for preparing the tissue constructs may include the alternate deposition of biodegradable polylactic acid (PLA) fibers and cell-laden gelatin methacrylate (GelMA) hydrogels. The presently disclosed methods may also include the regional immobilization of bioactive factors, such as bone morphogenetic protein 2 (BMP2) and vascular endothelial growth factor (VEGF) peptides, in the fabrication of the tissue construct in order to promote osteogenesis and angiogenesis through biocompatible mussel-inspired adhesion and "thiol-ene" click reactions. The presently disclosed methods may also include perfusion culture in a bioreactor system. The bioreactor system may be used to provide a dynamic biochemical environment for controlled and continuous stimulation of vascularized bone regeneration, thereby accelerating human endothelial cell and mesenchymal stem cell (hMSC) differentiation toward more rapid formation of vessel networks, and supporting long-term bone remodeling. The presently disclosed methods are capable of generating highly osteogenic tissue constructs with organized vascular networks that mimic human active bone.

The presently disclosed vascularized bone mimic constructs may have a biphasic structure in order to mimic the hierarchical structure and functionality of human native bone. The biphasic structure of the constructs includes a scaffold of high mechanical strength that mimics the mineralized component of native bone integrated with a vascular network of high flexibility.

According to at least one aspect of the present disclosure, a vascularized biphasic biomimetic tissue construct is provided. The tissue construct may include a scaffold having one or more channels as well as a vascular portion at least partially disposed in the one or more channels. The vascular portion may include a hydrogel. The tissue construct may also include a first bioactive growth factor and a second bioactive growth factor that is different from the first bioactive growth factor. The first bioactive growth factor may be localized to the scaffold while the second bioactive growth factor may be localized to the vascular portion of the tissue construct.

In at least some instances, the first bioactive growth factor may be bone morphogenetic protein 2 (BMP2) peptide and the second bioactive growth factor may be vascular endothelial growth factor (VEGF) peptide. In such cases, the bone morphogenetic protein 2 (BMP2) peptide may be immobilized on a surface of the scaffold. In some instances, the scaffold may comprise biodegradable polylactic acid (PLA) fibers. In some cases, the scaffold may be coated with polydopamine (pDA). In at least some instances, the scaffold may be made of a material having a compression modulus from about 0.03 to about 0.6 GPa.

In at least some instances, the hydrogel may be a gelatin methacrylate (GelMA) hydrogel. The hydrogel may include vascular endothelial growth factor (VEGF) peptides covalently conjugated to the hydrogel using a thiol-ene click reaction. The tissue construct, in at least some instances, may comprise from about 10% to about 30% hydrogel by weight. In some instances, the hydrogel may further include one human mesenchymal stem cells (hMSCs) and/or human umbilical vein endothelial cells (HUVECs). In some cases, the scaffold may be seeded with human mesenchymal stem cells (hMSCs).

According to at least one aspect of the present disclosure, a method of fabricating a biphasic tissue construct is provided. The method may include generating a scaffold having one or more channels and depositing a first bioactive growth factor on a surface of the scaffold. The method may further include seeding the scaffold with human mesenchymal stem cells (hMSCs) and forming a vascular portion at least partially disposed in the one or more channels in order to form a biphasic construct. The vascular portion may include a hydrogel, a second bioactive growth factor and one or more selected from the group consisting of human mesenchymal stem cells (hMSCs) and human umbilical vein endothelial cells (HUVECs). In at least some instances, the first bioactive growth factor may be bone morphogenetic protein 2 (BMP2) peptide and the second bioactive growth factor may be vascular endothelial growth factor (VEGF) peptide. In at least some instances, the scaffold may comprise biodegradable polylactic acid (PLA) fibers and the hydrogel may be a gelatin methacrylate (GelMA) hydrogel.

In at least some instances, the method may further include immobilizing the bone morphogenetic protein 2 (BMP2) peptide on a surface of the scaffold using biocompatible mussel-inspired chemistry and causing the vascular endothelial growth factor (VEGF) peptides to be covalently conjugated to the hydrogel using a thiol-ene click reaction. The method may also include, in some instances, coating the surface of the scaffold with polydopamine (pDA). The method may also optionally include forming a lumen structure in the vascular portion using a subtractive needle technique. In some instances, the method may also include incubating the biphasic construct in a bioreactor to promote vascularization and osteogenesis. In some cases, the scaffold may be generated using a fused deposition modeling (FDM) 3D bioprinter and the vascular portion may be formed using a stereolithography (SLA) 3D bioprinter.

According to at least one aspect of the present disclosure, a system is provided. The system may include a biphasic tissue construct comprising a scaffold having one or more channels and seeded with one or more human mesenchymal stem cells (hMSCs) and a first bioactive growth factor immobilized on a surface of the scaffold. The system may also include a vascular portion at least partially disposed in the one or more channels. The vascular portion may include a hydrogel, a second bioactive growth factor different from the first bioactive growth factor, and human mesenchymal stem cells (hMSCs) and/or human umbilical vein endothelial cells (HUVECs). The system may also include a bioreactor configured to promote vascularization and osteogenesis in the biphasic tissue construct.

As depicted in FIG. 1, the tissue construct may be fabricated through a dual 3D bioprinting method 100 based on the FDM and SLA bioprinter systems. First, a hard scaffold portion 110 is generated using a fused deposition modeling (FDM) 3D bioprinter system 120 to produce stacked units, each with a honeycombed pore shape so as to produce channels (e.g., canals and lamellae) so as to mimic the osteon and/or haversian system in native bone. The channels generated by the 3D printing process provides vascularization in the form of channels in the scaffold. According to at least one aspect of the present disclosure, the scaffold may have a plurality of channel sizes. In at least some instances, the scaffold may include a central channel having a diameter from about 500 µm to about 2000 µm, or from about 1200 µm to about 1800 µm, or from about 750 µm to about 1750 µm, or from about 750 µm to about 1500 µm, or from about 1000 µm to about 2000 µm, or from about 1000 µm to about 1500 µm, or from about 1250 µm to about 1750 µm, or from about 1500 µm to about 2000 µm. The scaffold may also have a plurality of peripheral channels having a diameter from about 20 µm to about 200 µm, or from about 20 to about 50 µm, or from about 25 µm to about 35 µm, or from about 20 µm to about 75 µm, or from about 20 µm to about 100 µm, or from about 50 µm to about 150 µm, or from about 50 µm to about 200 µm, or from about 100 µm to about 200 µm, or from about 150 µm to about 200 µm, or from about 175 µm to about 200 µm. In at least some cases, the scaffold may include a plurality of central channels having a diameter from about 500 µm to about 2000 µm and a plurality of peripheral channels having a diameter from about 20 µm to about 200 µm.

The scaffold may also have an average pore size of from about 50 µm to about 300 µm, or from about 50 µm to about 100 µm, or from about 50 µm to about 250 µm, or from about 75 µm to about 250 µm, or from about 125 µm to about 300 µm, or from about 150 µm to about 300 µm, or from about 175 µm to about 300 µm, or from about 200 µm to about 300 µm, or from about 225 µm to about 275 µm. The scaffold may also have a porosity of between about 10% to about 40%, or from about 15% to about 35%, or from about 20% to about 40%, or from about 15% to about 25%, or from about 15% to about 30%.

The scaffold may be a hard material having a compression modulus from about 0.03 to about 0.6 GPa. The scaffold may be a material that may degrade in the human body following implantation. In at least some instances, the scaffold may comprise biodegradable polylactic acid (PLA) fibers. In other cases, the scaffold may comprise polycaprolactone (PCL), or poly(lactic-co-glycolic acid) (PLGA). In some cases, the scaffold may comprise any combination of polylactic acid (PLA), polycaprolactone (PCL), and poly(lactic-co-glycolic acid) (PLGA).

Additional vascularization in the scaffold structure may develop as a result of seeding the scaffold, including the surfaces of the channels in the scaffold, with hMSCs for further osteogenesis. It has been found that endothelial cells tend to assemble into capillary-like and lumen-like structures that can generate functional vasculature in 3D constructs prepared according to the presently disclosed methods and techniques.

Even further vascularization may develop in the scaffold structure due to biodegradation of the scaffold during incubation in a bioreactor or following human implantation. After human implantation, the regenerated bone may grow, develop, and remodel while the PLA scaffold degrades.

As depicted in FIG. 1, cell-laden gelatin methacrylate (GelMA) hydrogels may then be generated and printed 130 onto the scaffold having 3D printed vascular channels 110 using an SLA bioprinter system to produce a vascularized biphasic tissue construct 150 that mimics native bone structure. In at least some instances, the intracavity spaces within the whole bone region are penetrated with the endothelial cell-laden elastic hydrogel, facilitating the formation of capillary-like networks and vascular lumen-like channels. Tubular hydrogels may be fabricated via annular printing within the interconnected vascular channels to provide an uninhibited fluid environment and vascular invasion spaces in vivo. In other cases, method 100 may include alternate deposition of biodegradable polylactic acid (PLA) fibers and cell-laded gelatin methacrylate (GelMA) hydrogels. In such cases, a first PLA unit having channels is prepared using the FDM bioprinter system. The channels of the first PLA unit are then infilled with a cell-laden gelatin methacrylate (GelMA) hydrogel using a SLA bioprinter system. Subsequently, a second PLA unit is printed on top of the first PLA unit followed by deposition of the hydrogel into the channels of the second PLA unit. In this manner, any number of PLA units may be prepared by having channels filled with hydrogel to prepare a vascularized biphasic tissue construct 150 by alternate deposition of PLA fibers and cell-laden hydrogels.

Figure 2:
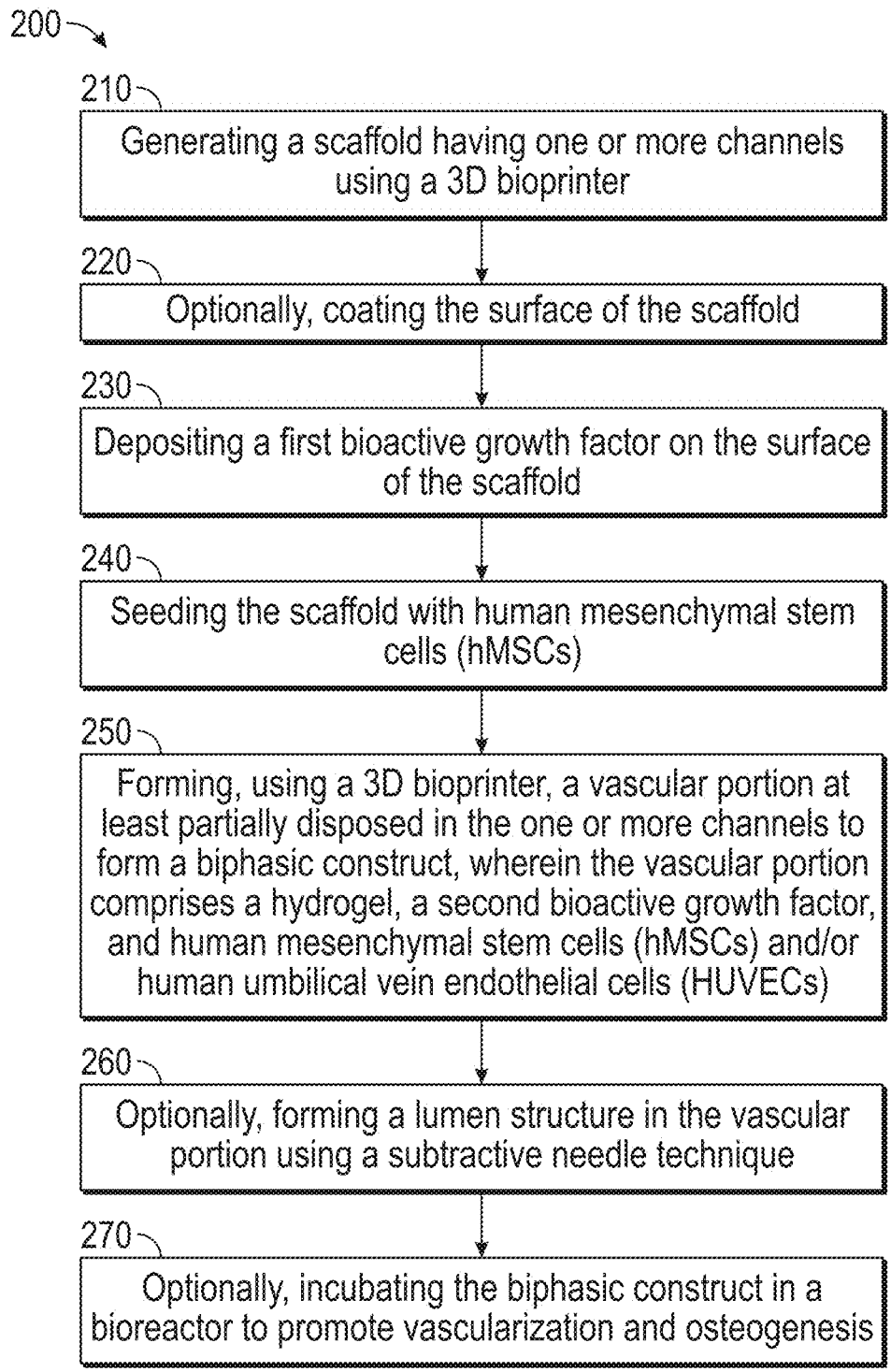
FIG. 2 is a flowchart describing a method of preparing a vascularized biphasic biomimetic tissue construct, according to an exemplary embodiment of the present disclosure.

Referring to FIG. 2, a flowchart is presented in accordance with an example embodiment of the present disclosure. The example method shown in FIG. 2 is provided by way of an example, as there are a variety of ways to carry out the method. Each block shown in FIG. 2 represents one or more processes or methods carried out in the example method shown in FIG. 2. Furthermore, the illustrated order of blocks is illustrative only and the order of the blocks can change according to the present disclosure. Additional blocks can be added or fewer blocks can be utilized, without departing from this disclosure.

Method 200 depicted in FIG. 2 is an example method that may be used to prepare the presently disclosed biphasic tissue constructs. The method 200 depicted in FIG. 2 is just an example method and can be adopted to other operating environments by adding or removing one or more blocks. The example method 200 can begin at block 210. At block 210, a scaffold having one or more channels is generated using a 3D bioprinter. In at least some instances, the scaffold may be formed of biodegradable polylactic acid (PLA) fibers and generated using a a fused deposition modeling (FDM) 3D bioprinter. At block 220, the method 200 may optionally further include coating the surface of the scaffold. For example, the scaffold may be coated with polydopamine (pDA). At block 230, the method 200 may further include depositing a first bioactive growth factor on the surface of the scaffold. In some instances, the first bioactive growth factor may be bone morphogenetic protein 2 (BMP2) peptide. In such cases, BMP2 peptides may be immobilized on the surface of the scaffold using biocompatible mussel-inspired chemistry, such as that described in more detail below. The first bioactive growth factor may be deposited and/or immobilized on any surface of the scaffold including portions of the scaffold comprising a wall of the channels formed in the scaffold. In at least some instances, the first bioactive growth factor may be primarily localized to the walls of the channels formed in the scaffold.

At block 240, the method 200 further includes seeding the scaffold with human mesenchymal stem cells (hMSCs). Method 200 further includes, at block 250, forming, using a 3D bioprinter, a vascular portion at least partially disposed in the one or more channels of the scaffold in order to form a biphasic construct. The vascular portion includes a hydrogel. In at least some instances, the vascular portion may be formed using a stereolithography (SLA) 3D bioprinter. The vascular portion may also include a second bioactive growth factor and human mesenchymal stem cells (hMSCs) and/or human umbilical vein endothelial cells (HUVECs). In at least some instances, the hydrogel may be a gelatin methacrylate (GelMA) hydrogel. In some cases, the second bioactive growth factor may be vascular endothelial growth factor (VEGF) peptide. In such cases, the VEGF may be covalently conjugated to the hydrogel using a thiol-ene click reaction.

At block 260, method 200 may optionally further include forming a lumen structure in the vascular portion of the biphasic tissue construct using a subtractive needle technique. At block 270, method 200 may also optionally further include incubating the biphasic construct in a bioreactor, such as the bioreactor shown in FIG. 13, in order to promote vascularization and osteogenesis in the tissue construct, as described in more detail below.

Figure 3:
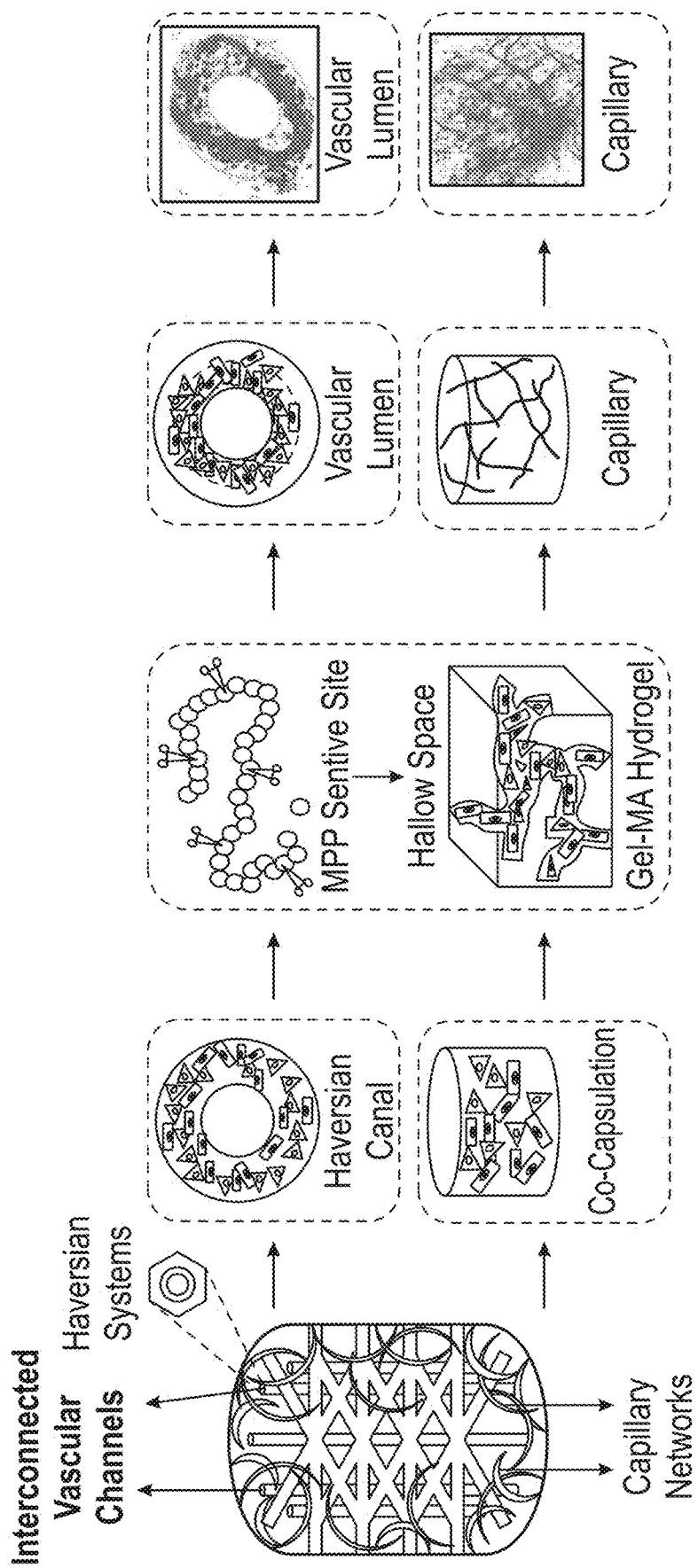
FIG. 3 is a schematic representation of the microstructural design features of presently disclosed vascularized biphasic tissue constructs prepared according to the presently disclosed methods using MMP sensitive GelMA hydrogels and having vascular lumen and capillary network formation achieved at different regions during the culture period, according to an exemplary embodiment of the present disclosure.

Controlling the biological and physicochemical properties of the hydrogel is critical for manipulating cell behaviors and therefore for fabricating functional tissue constructs. Considering the complex nature of the native extracellular matrix (ECM), dynamic hydrogels could provide an effective framework for cells to respond to environmental signals over time with appropriate spatial resolution. GelMA hydrogels have matrix metalloprotease (MMP) sensitive sequences which can be cleaved by MMP secretion from endothelial cells. In construct, the capillary structure can be formed via a cord hollowing mechanism, with evolution and expansion of intercellular space in the GelMA hydrogel network during the culture period, as shown in FIG. 3. It has been found that biphasic tissue constructs prepared according to the presently disclosed methods have advantageous stability when the hydrogel polymer solution concentration is at least 5 wt %. In at least some instances, the presently disclosed biphasic tissue constructs may be prepared using a hydrogel polymer solution having a hydrogel polymer solution concentration of from about 5 wt % to about 30 wt %, or from about 10 wt % to about 15 wt % hydrogel, or from about 10% to about 20% hydrogel.

Figure 4:
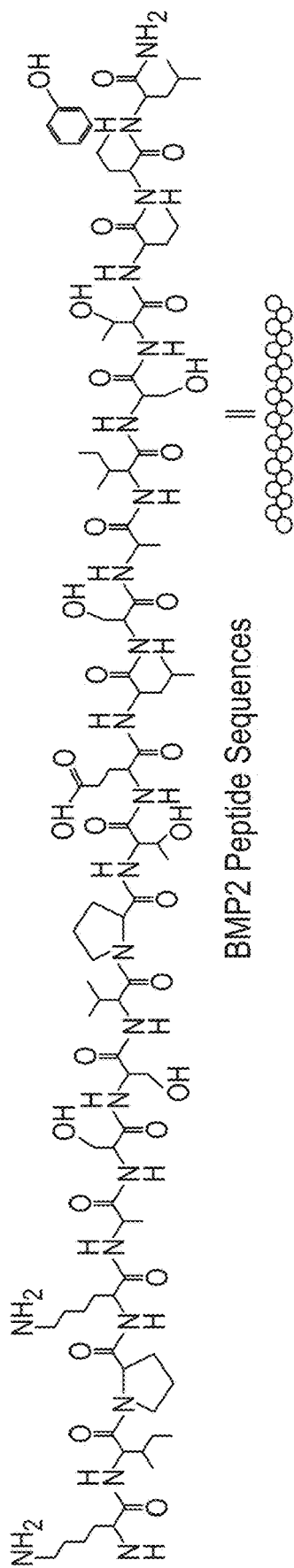
FIG. 4 is a schematic representing the chemical structure of a BMP2-mimetic peptide, according to an exemplary embodiment of the present disclosure.
Figure 5:
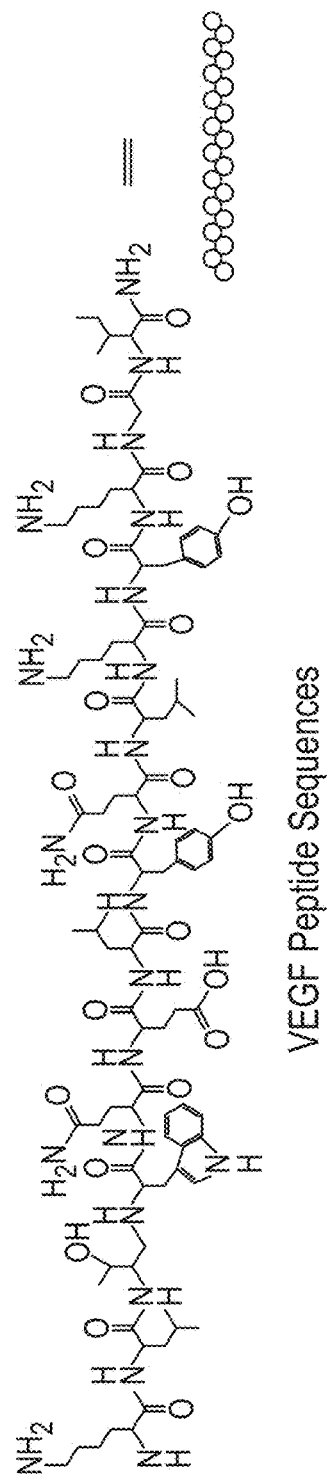
FIG. 5 is schematic representing the chemical structure of a VEGF-mimetic peptide, according to an exemplary embodiment of the present disclosure.
Figure 6:
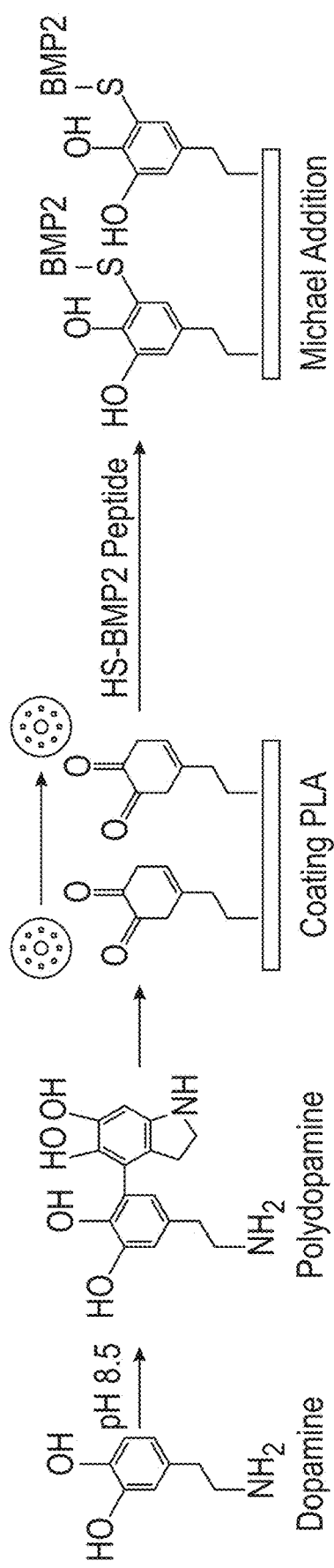
FIG. 6 is a schematic of the biocompatible mussel-inspired chemistry used to regionally immobilize BMP2 during PLA scaffold fabrication, according to an exemplary embodiment of the present disclosure.
Figure 7:
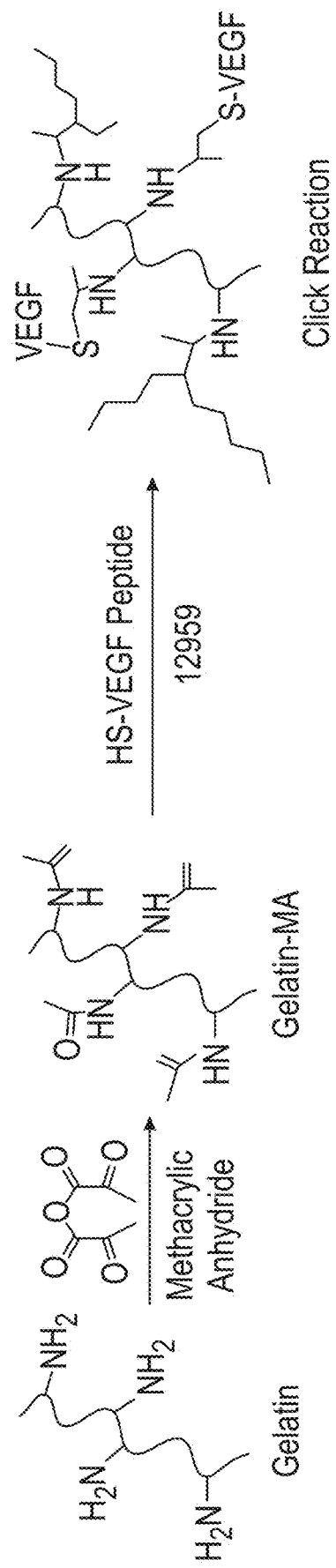
FIG. 7 is a schematic of the "thiol-ene" click reaction used to regionally immobilize VEGF peptides during SLA printing of GelMA hydrogel, according to an exemplary embodiment of the present disclosure.

The mechanisms of angiogenesis and osteogenesis during bone regeneration and regulation involves complex cascades of signaling pathways. While some investigators have attempted to utilize those signaling processes to direct cellular behavior in vitro through the delivery of exogenous growth factors, targeted transport and sustained release of growth factors with time- and dose-dependent kinetics is difficult to implement in current clinical research. In addition, short half-life for bioactivity and high cost has restricted their commercial success. Low-cost bioactive peptides derived from the knuckle epitopes growth factors have been developed as a functional analogue to regulate cellular events. The peptide sequences, KIPKASSVPTELSAIST-LYLNH2 and KLTWQELYQLKYKGINH2, as shown in FIGS. 4 and 5, respectively represent specific receptor-binding domains of BMP2 and VEGF, which have been verified to effectively promote osteogenesis and angiogenesis through activating signaling receptors. According to the present disclosure, thiol-functional oligopeptides were designed based upon these peptide sequences to facilitate further immobilization. This potentially addresses issues for prolonged tissue retention and sustainable bioactivity of released factors, as well as site specific delivery to regenerated tissue. During the fabrication process, an integrated manufacturing technique, which combines mussel-inspired chemistry on PLA scaffolds and "thiol-ene" click reaction in hydrogels (see FIGS. 6 and 7), was performed to enable regional induction during complex tissue regeneration. The mussel-inspired chemistry and click reaction offered non-toxic and efficient methods for the preparation of multicomponent conjugated constructs. It has been unexpectedly found that these stereo-arrangement epitopes within bioconjugative 3D hydrogels can enhance the configuration-dependent signaling of the VEGF receptors.

Figure 8:
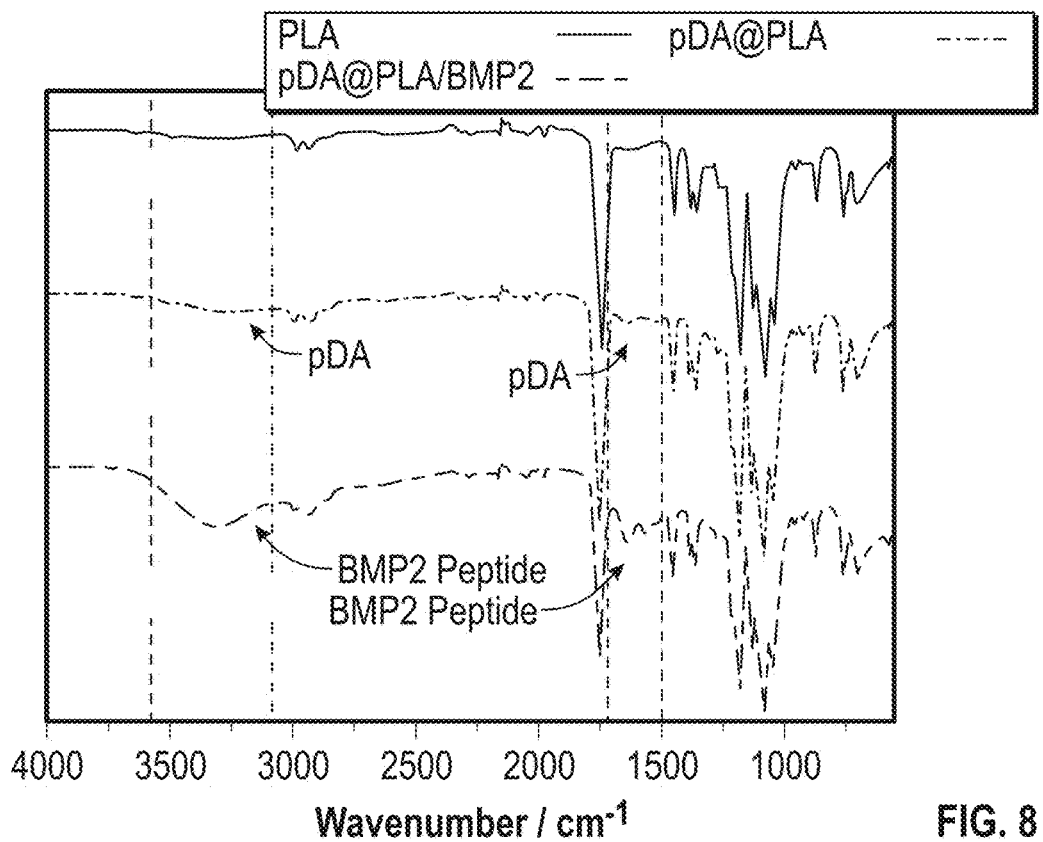
FIG. 8 depicts ATR-FTIR spectra of PLA scaffold, pDA coated scaffold and BMP2 immobilized scaffold, according to an exemplary embodiment of the present disclosure.
Figure 9:
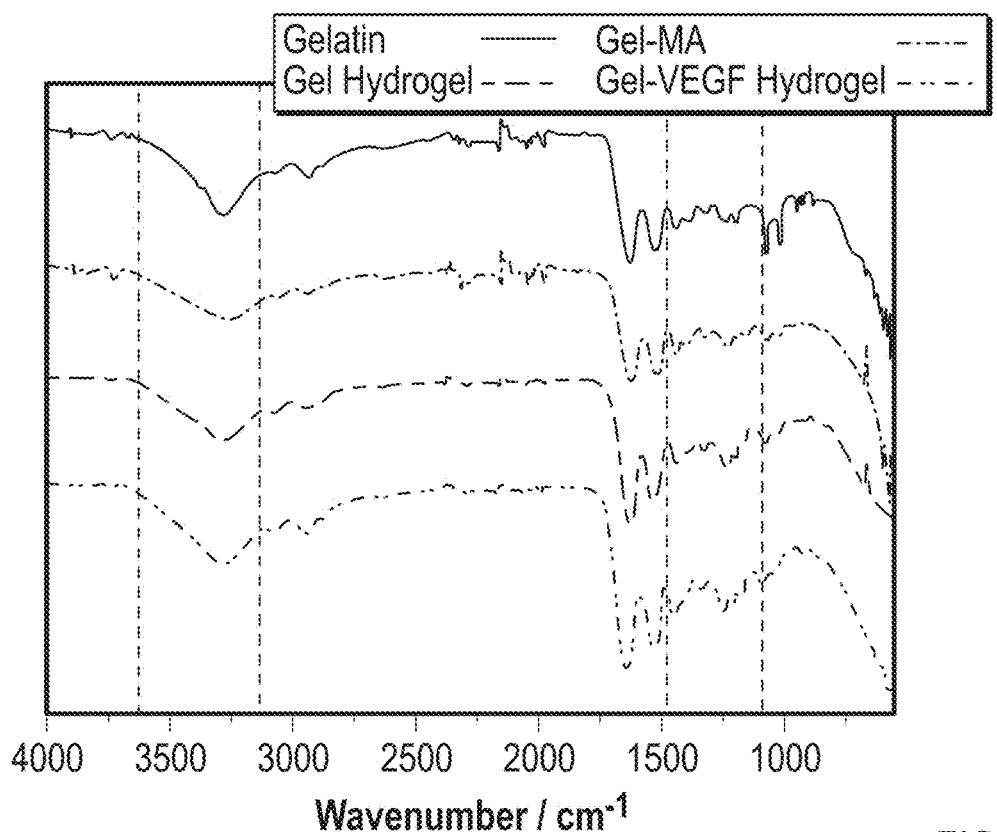
FIG. 9 depicts ATR-FTIR spectra of Gelatin, GelMA, Gel hydrogel and Gel-VEGF immobilized hydrogel, according to an exemplary embodiment of the present disclosure.
Figure 10:
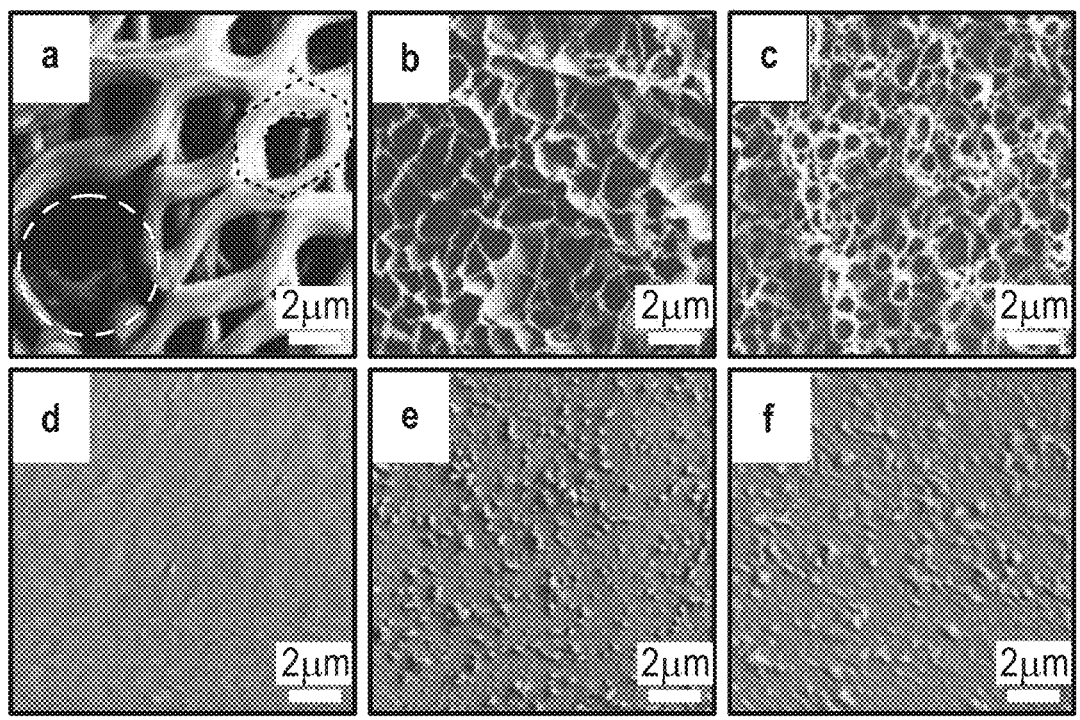
FIG. 10 depicts Scanning Electron Microscope (SEM) micrographs showing microstructural characterization of biphasic constructs, according to an exemplary embodiment of the present disclosure, with micrograph (a) showing a hard bone scaffold (the circle shows 500 µm vascular channels and the smaller circle shows 200 µm pores with a 200 µm scale bars indicating scale, micrograph (b) showing a lyophilized 10 wt % GelMA hydrogel by 3D bioprinting with a 10 µm scale bar indicating scale, micrograph (c) showing a lyophilized 20 wt % GelMA hydrogel by 3D bioprinting with a 10 μm scale bar indicating scale, micrograph (d) showing the surface morphology of an untreated PLA scaffold with a 2 μm scale bar indicating scale, micrograph (e) showing the surface morphology of a pDA coated scaffold with a 2 μm scale bar indicating scale, and micrograph (f) showing the surface morphology of a BMP2 immobilized scaffold with a 2 μm scale bar indicating scale.
Figure 21:
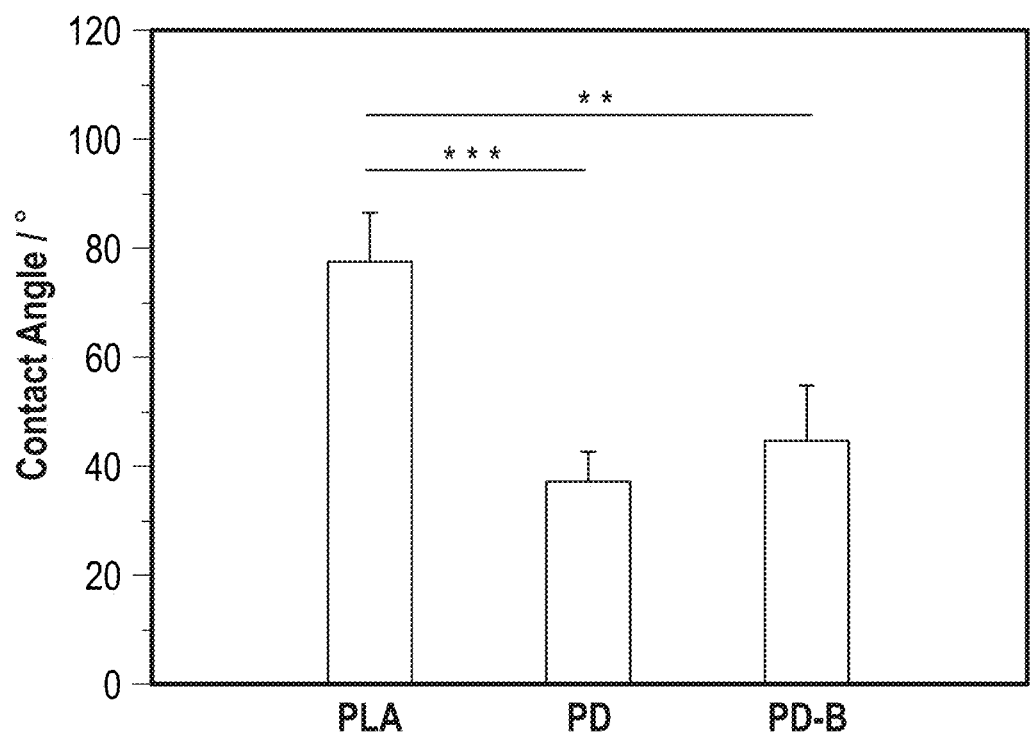
FIG. 21 is a data plot showing contact angle measurement of different scaffold materials, according to an exemplary embodiment of the present disclosure.
Figure 22:
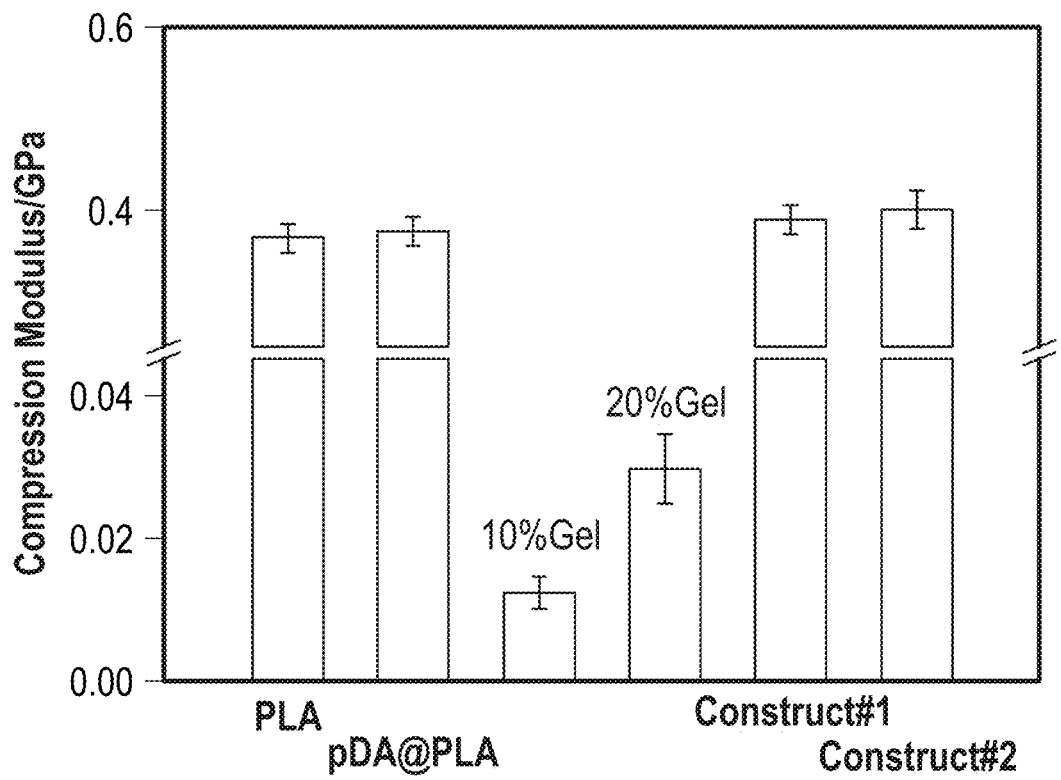
FIG. 22 is a data plot depicting mechanical properties of 3D bioprinted scaffolds, bulk hydrogels and constructs, and indicating that after fabrication, constructs maintained native bone-like mechanical strength, according to an exemplary embodiment of the present disclosure.

ATR-IR spectroscopy confirmed the successful polydopamine (pDA) coating and effective immobilization of BMP2 peptides on the surface of 3D bioprinted PLA scaffolds, as well as covalent conjugation of VEGF peptides in the GelMA hydrogel, as shown in FIGS. 8 and 9. The hydrophilicity of the pDA coated scaffolds (PD) exhibited a significant increase compared with the hydrophobic PLA scaffolds. Additionally, the wettability showed unobvious changes after BMP2 peptide immobilization (PD-B), as shown in FIG. 21. In comparison to smooth and featureless PLA, SEM images revealed a nanoscale granular feature uniformly distributed over the PD scaffold's surface, and the immobilization of BMP2 peptides distinctively increased the size of the granules. The morphological characteristics of lyophilized GelMA hydrogel (Gel) illustrated an inner regular network structure that could be beneficial to the exchange of nutrients for cell viability; the higher concentration hydrogel showed more compact networks, as shown in FIG. 10. The VEGF immobilization (Gel-V) did not induce any changes in the hydrogel's morphology (not shown). In addition, our 3D bioprinted constructs also displayed disparate mechanical properties by region. They possessed a native bone-like mechanical strength in the bone region, with a compressive modulus of about 0.38 GPa; whereas in the vascular region the elastic modulus increased from 10 to 30 kPa with increasing concentration providing an appropriate microenvironment for cell encapsulation, as shown in FIG. 22. Additionally, the peptide immobilization could serve as one of the most available strategies for modulating cellular events.

Figure 11:
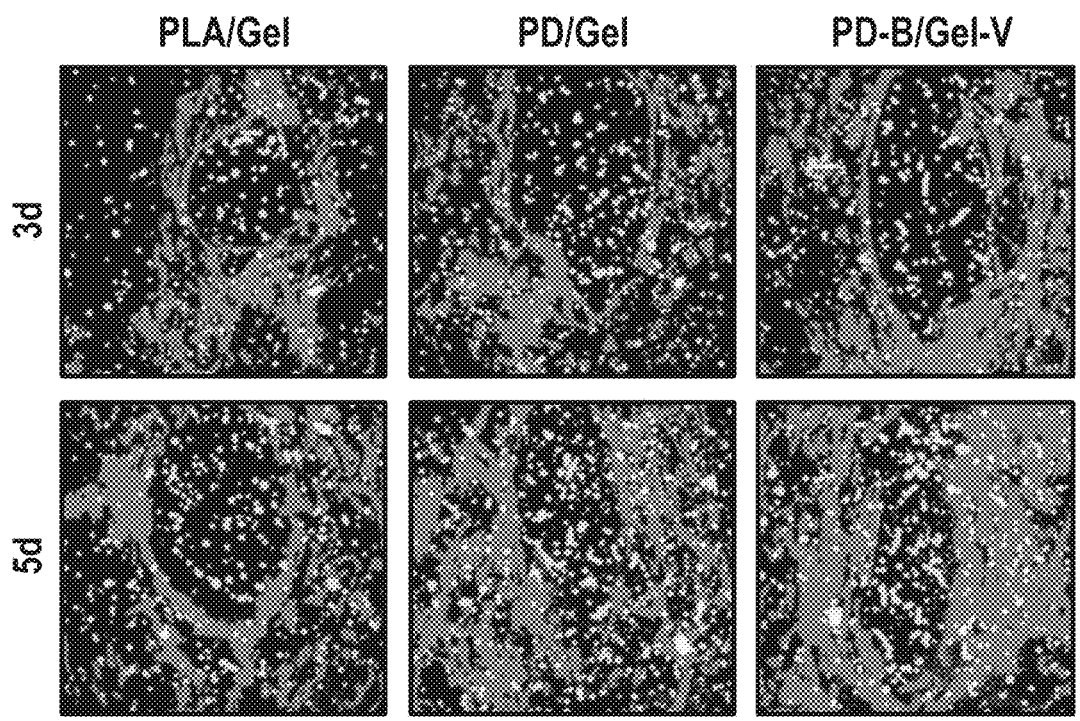
FIG. 11 depicts images of cell laden vascularized bone constructs, specifically confocal fluorescence images of co-cultured hMSCs and HUVECs in biphasic constructs for 3d and 5d with a 100 μm scale bar indicating scale (hMSCs are labeled with cell tracker red while HUVECs are stained with cell tracker green), according to an exemplary embodiment of the present disclosure.
Figure 12:
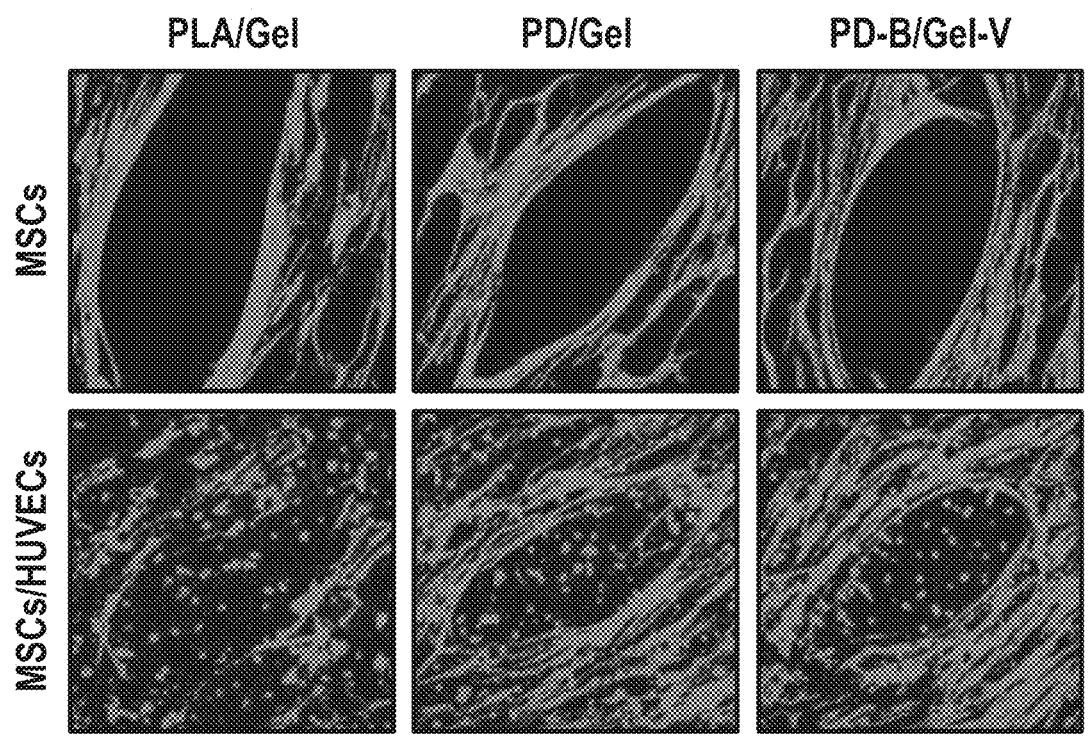
FIG. 12 depicts images of cell laden vascularized bone constructs, specifically fluorescent images of hMSCs and HUVECs in the biphasic structural constructs with F-actin (red) and nucleus (blue) staining showing that the hMSCs exhibited a well distributed spreading on the scaffold surface, while the HUVECs and hMSCs encapsulated in hydrogel formed rounded morphology with a 100 μm scale bar indicating scale, according to an exemplary embodiment of the present disclosure.
Figure 23:
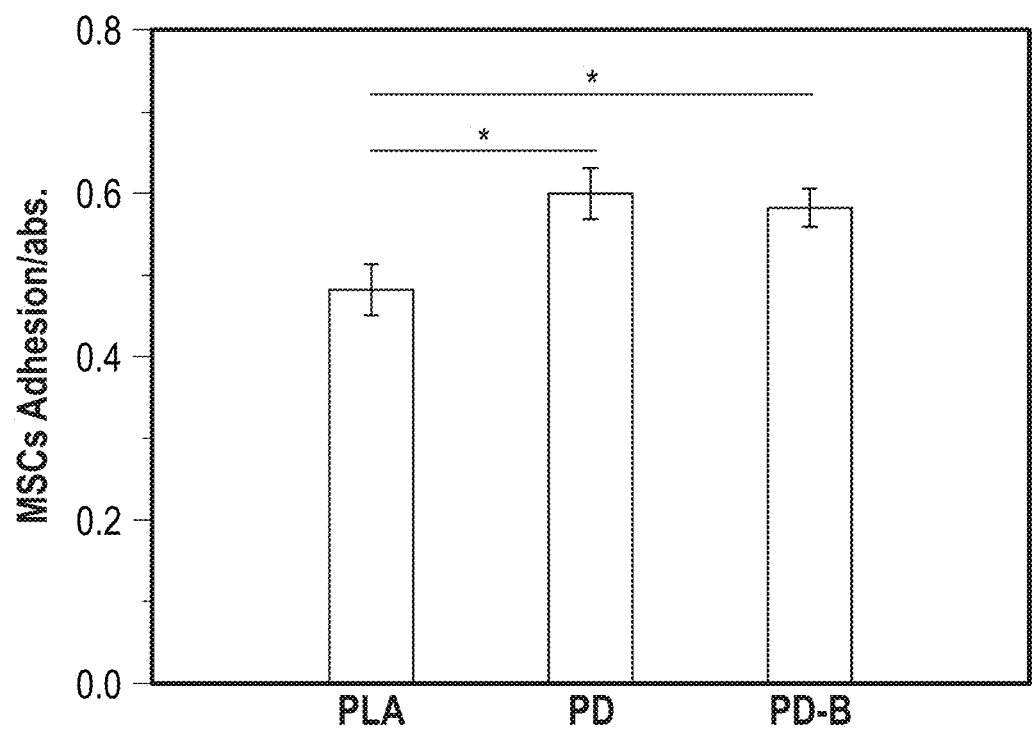
FIG. 23 is a data plot showing hMSCs adhesion during seeding on different scaffolds, according to an exemplary embodiment of the present disclosure.
Figure 24:
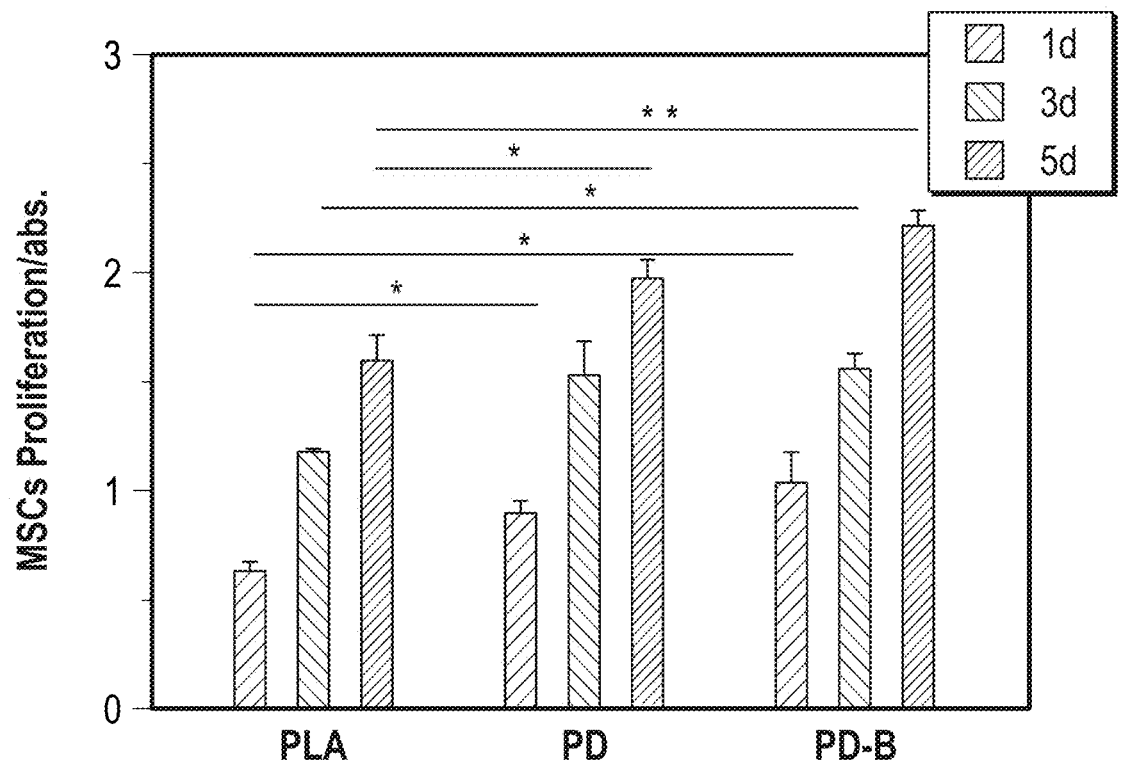
FIG. 24 is a data plot showing hMSCs proliferation after seeding on different scaffolds, according to an exemplary embodiment of the present disclosure.
Figure 25:
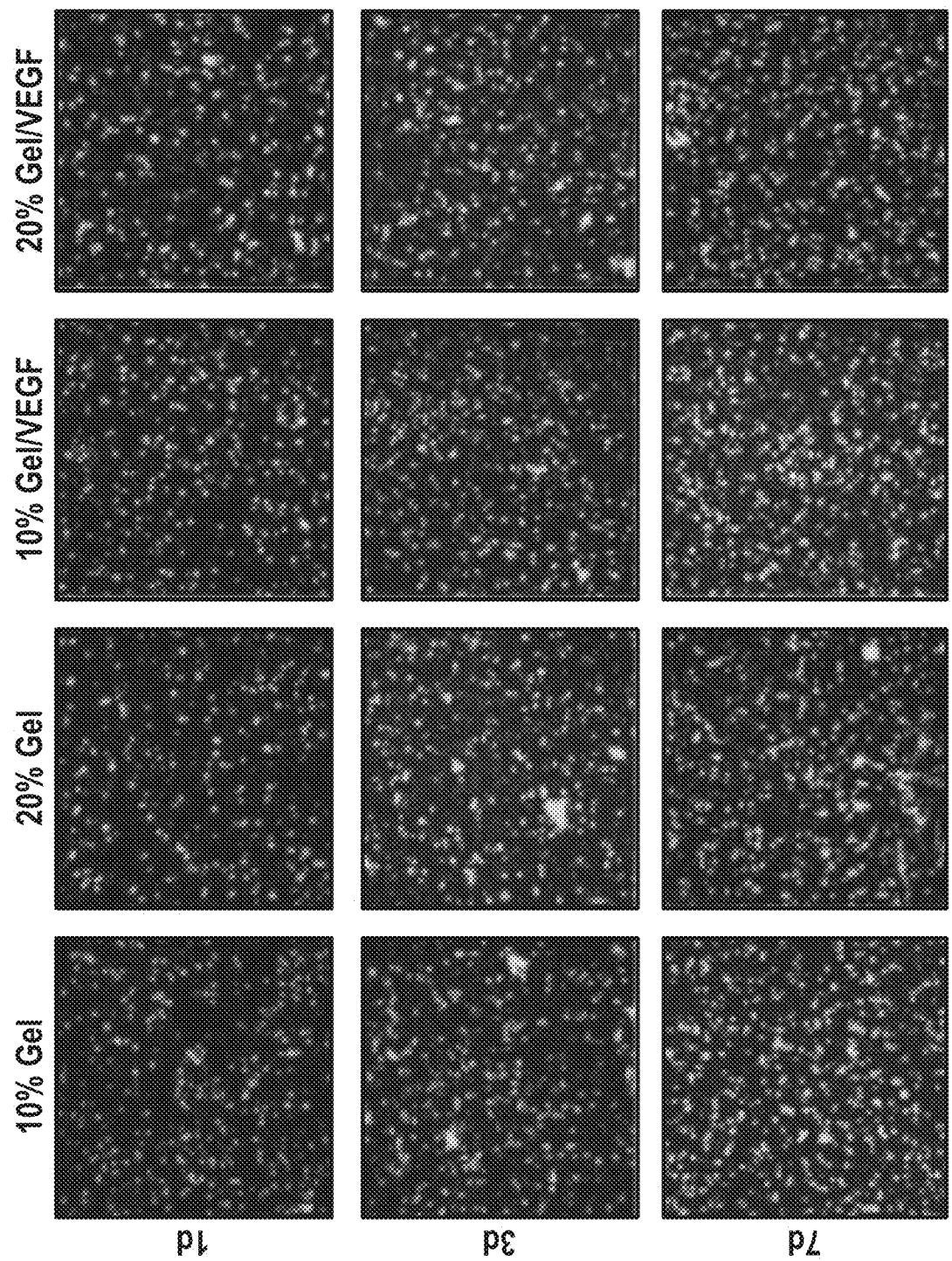
FIG. 25 is a set of images depicting live/dead staining of HUVECs encapsulated in 3D bioprinted hydrogels with different concentration, according to an exemplary embodiment of the present disclosure.
Figure 26:
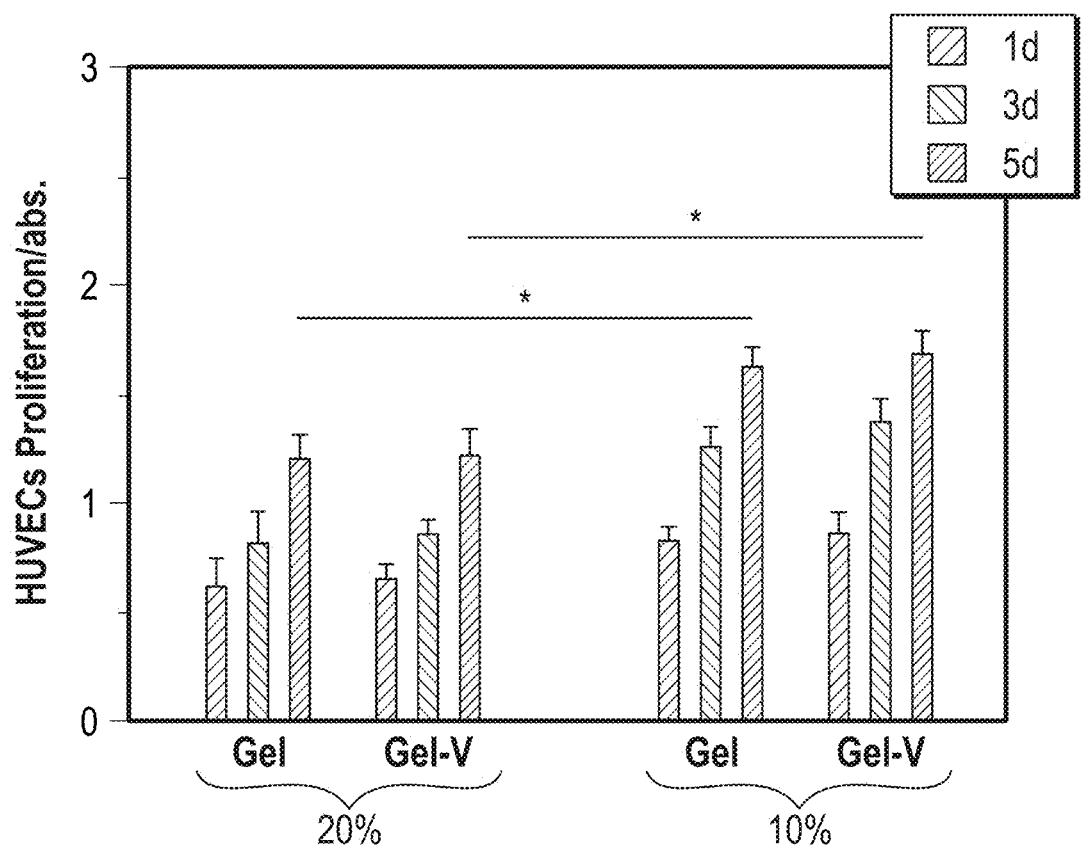
FIG. 26 is a data plot showing proliferation of HUVECs encapsulated in 3D bioprinted hydrogels with different concentration, according to an exemplary embodiment of the present disclosure.
Figure 27:
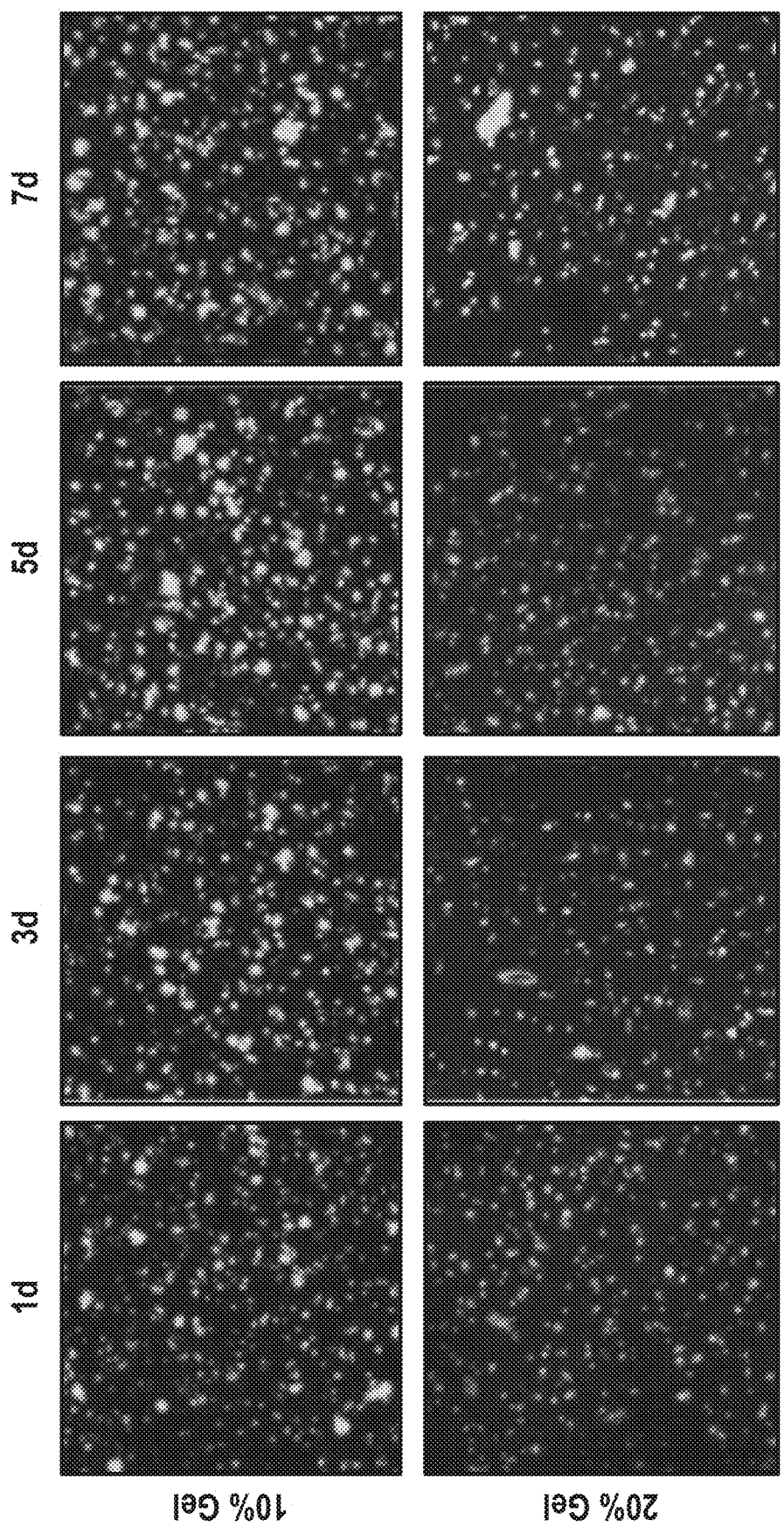
FIG. 27 is a set of images depicting live/dead staining of hMSCs encapsulated in 3D bioprinted hydrogels with different concentration, according to an exemplary embodiment of the present disclosure.
Figure 28:
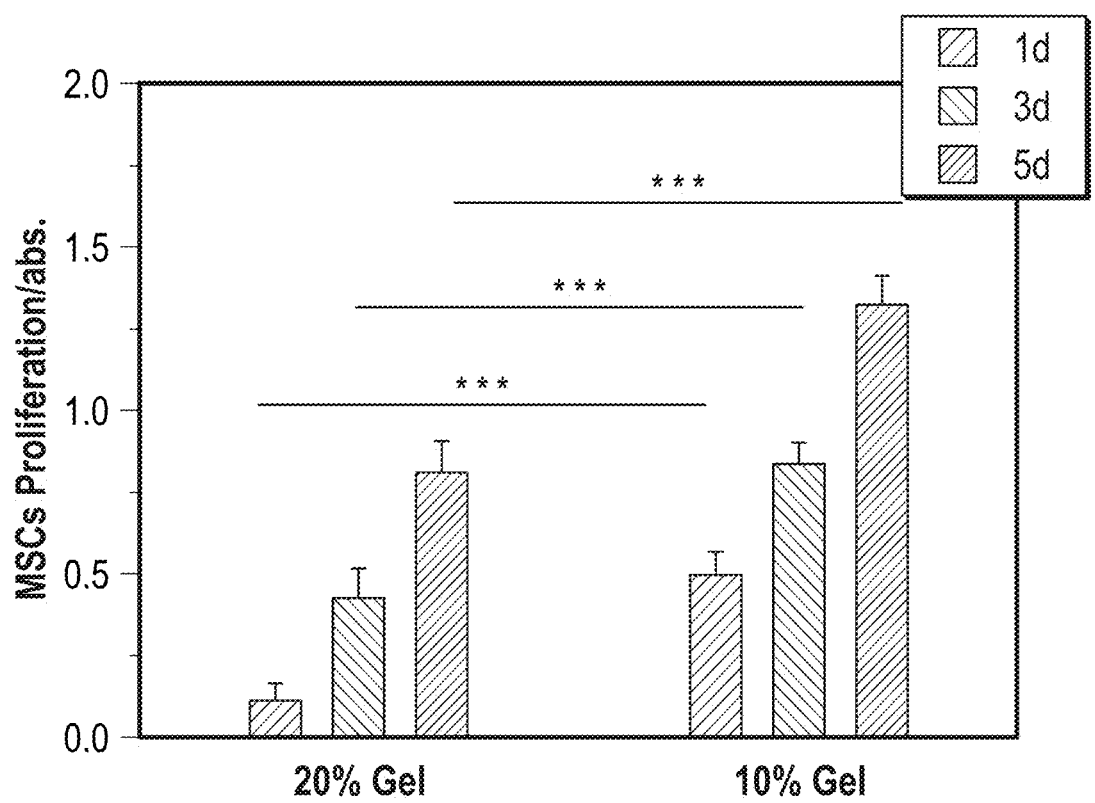
FIG. 28 is a data plot showing proliferation of hMSCs encapsulated in 3D bioprinted hydrogels with different concentration, according to an exemplary embodiment of the present disclosure.

In at least some instances, a "two-step" cell culture method may be used to prepare the biphasic tissue constructs. In such cases, the method includes the pre-seeding of hMSCs on PLA scaffolds and co-encapsulation of hMSCs and human umbilical vein endothelial cells (HUVECs) (1:1 ratio) in the GelMA hydrogel. 3D co-encapsulation of HUVECs and hMSCs will self-organize to form tubuar networks in the pro-vascular environment; the addition of hMSCs serves to stabilize the endothelial tubes. The hMSCs may be homogeneously distributed on the surface of the scaffolds, as shown in FIG. 11. The PD/Gel group and the PD-B/Gel-V group exhibited improved cell adhesion over other groups. Meanwhile, HUVECs were uniformly infused into the cavities of scaffolds when encapsulated in GelMA hydrogel. In order to reduce the interference of fluorescent signals, hMSCs were not stained red when encapsulated in hydrogel. Additionally, the quantitative results of hMSC adhesion and proliferation also confirmed that the PD-B scaffolds presented a superior cytocompatibility compared with pure PLA scaffolds, as shown in FIGS. 23 and 24. Viability and proliferation of encapsulated HUVECs and hMSCs was determined by live-dead staining and alamar blue assay, respectively. As shown in FIGS. 25-28, the staining of cultures after 1, 3 and 7 days indicated that the cell viability of both HUVECs and hMSCs was preserved and not significantly influenced in the GelMA hydrogel. Initial death of cells was observed on the first day due to UV laser exposure during curing. However, cell death was significantly reduced over prolonged culture periods. The quantitative data up to 7 days showed that 10 wt % hydrogel had higher proliferation activity, suggesting that a softer and looser environment might provide a preferable living space for encapsulated cell development. Biphasic tissue constructs having a vascular region fabricated using 10 wt % hydrogel were prepared. It was determined that such constructs having GelMA hydrogel provide more space for cell expansion and migration for endothelium development. Furthermore, F-actin staining showed that for pDA and BMP2 modified scaffolds, hMSCs spread well and maintained a normal polygonal morphology, as shown in FIG. 12. Meanwhile, HUVECs and hMSCs encapsulated in hydrogel formed rounded morphology due to the isotropic stress caused by the limited space.

Figure 13:
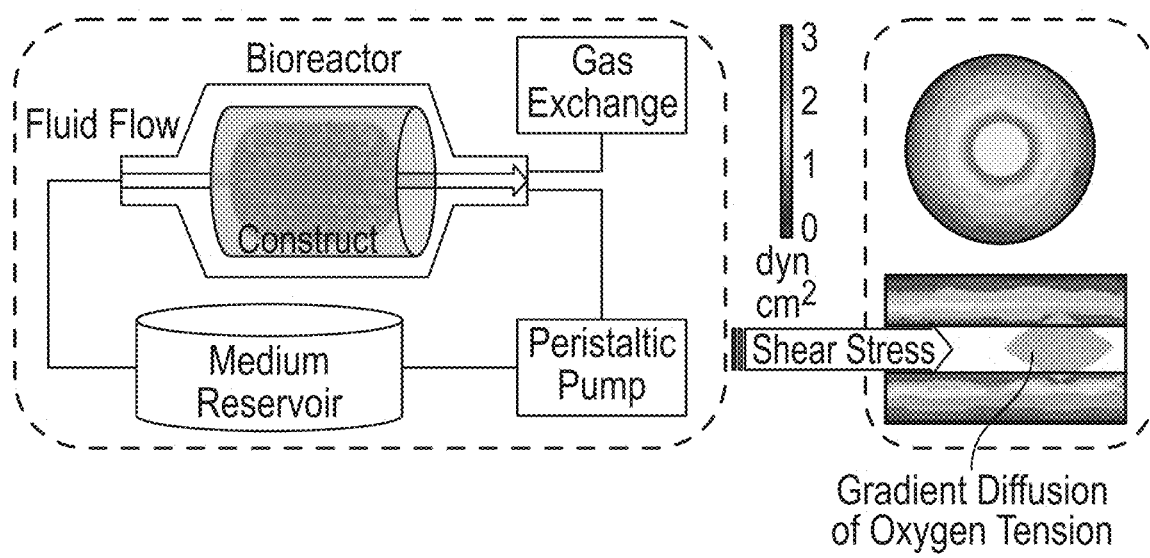
FIG. 13 depicts a schematic diagram of a system that includes a vascularized bipohasic biomimetic tissue construct in a flow bioreactor system, according to an exemplary embodiment of the present disclosure.

According to at least one aspect of the present disclosure, a flow bioreactor system may be used to mimic the native fluid environment in order to incubate the cells on the 3D bioprinted constructs to enhance the vascularization of the constructs in dynamic culture, as shown in FIG. 13. When culture medium flowed through constructs at a certain rate, cells encapsulated in hydrogel would be subject to fluid shear stress mimicking surrounding fluid present in vivo. FIG. 13 shows finite-element model predictions of shear stress, and a gradient diffusion control of oxygen tension. In order to reduce the fluid shear stress experienced by the cells encapsulated in the hydrogel in the incubated constructs, the flow bioreactor utilized a culture medium flow rate of 5 mL/min. Representative hydrodynamic parameters of permeability (KD) and average shear stress ($\tau$) were calculated using Darcy's Law and the modified Brinkman equation, respectively. It was determined that the average hydraulic permeability of the hydrogel region was $2.9 \times 10^{-7}$ cm$^2$, corresponding to a shear stress of approximately 2.4 dyn/cm$^2$. This value is within the range of venous shear stress noted in microcirculation. Despite the exposure of the incubated constructs to shear forces in the bioreactor, it was found that the use of a bioreactor as shown in FIG. 13, was beneficial as compared to slow permeation in static culture, by ensuring homogenous and efficient mass transport within the scaffolds and the scaffold channels. Furthermore, the mechanical cues, present at the onset of several signaling pathways in normal physiological conditions, have been shown to positively influence bone formation and vascularization as well as further integration.

Figure 14:
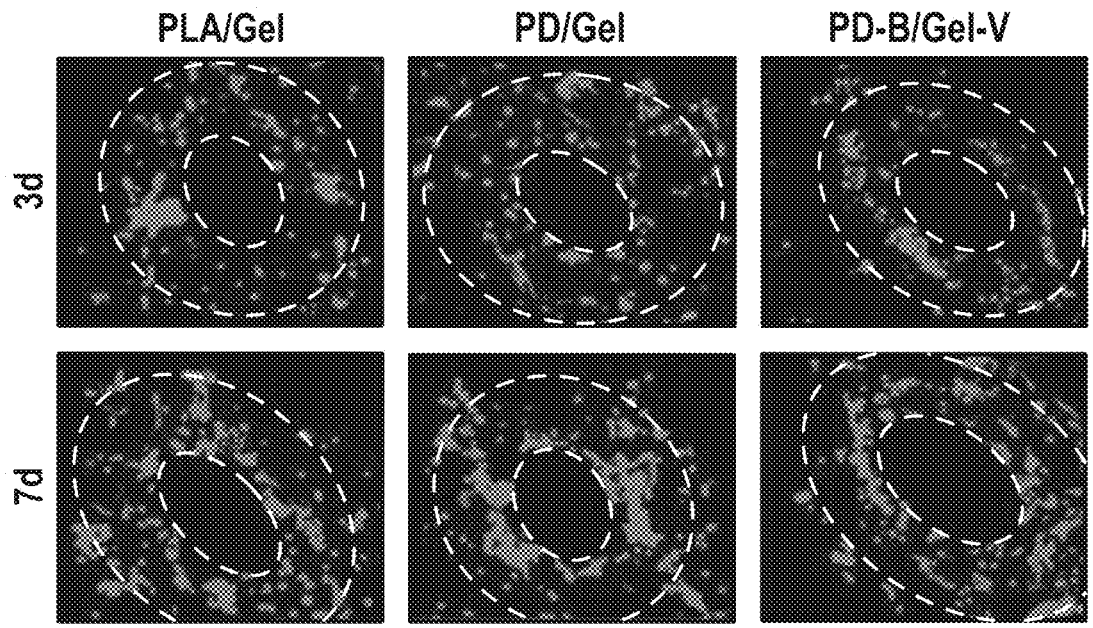
FIG. 14 depicts confocal fluorescence images of hMSCs and HUVECs co-culture (with 100 μm scale bar indicating scale) in designed vascular channel regions for 1 week demonstrating that HUVECs encapsulated in hydrogel were inclined to aggregate and migrate to form annular ring patterns along the channel, according to an exemplary embodiment of the present disclosure.
Figure 15:
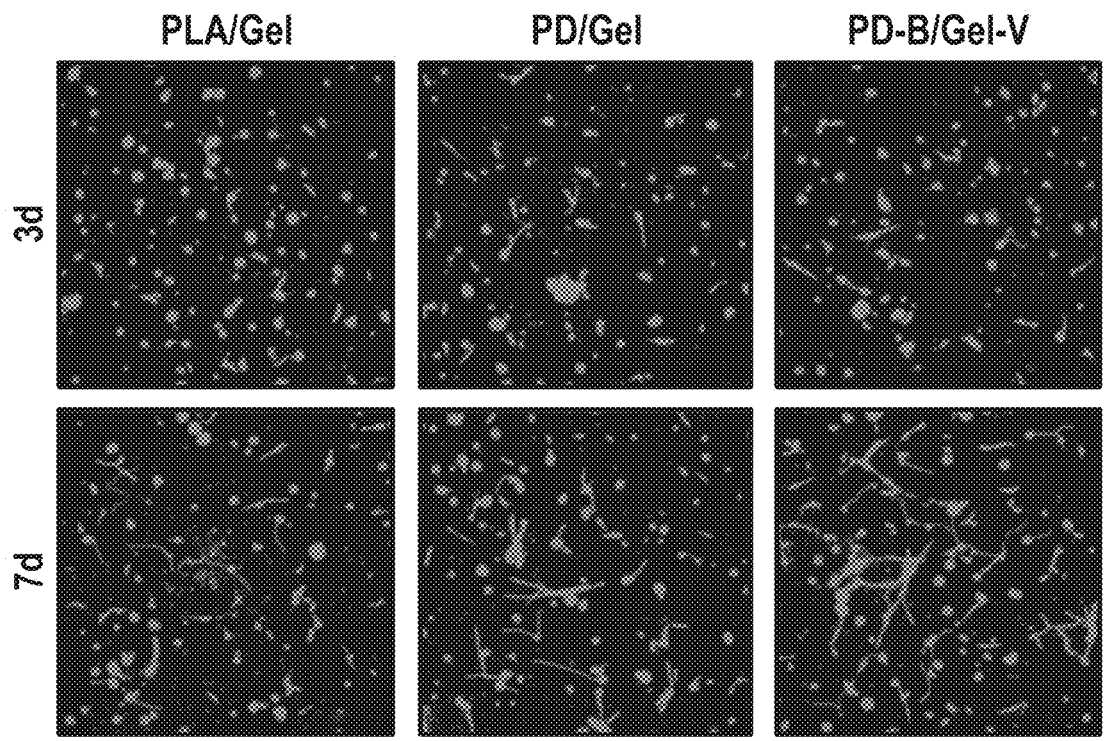
FIG. 15 depicts fluorescence images of hMSCs and HUVECs co-cultured in the hydrogel (with 100 μm scale bar indicating scale) clearly revealing extensive capillary networks formed within all constructs at 7 days, according to an exemplary embodiment of the present disclosure.
Figure 16:
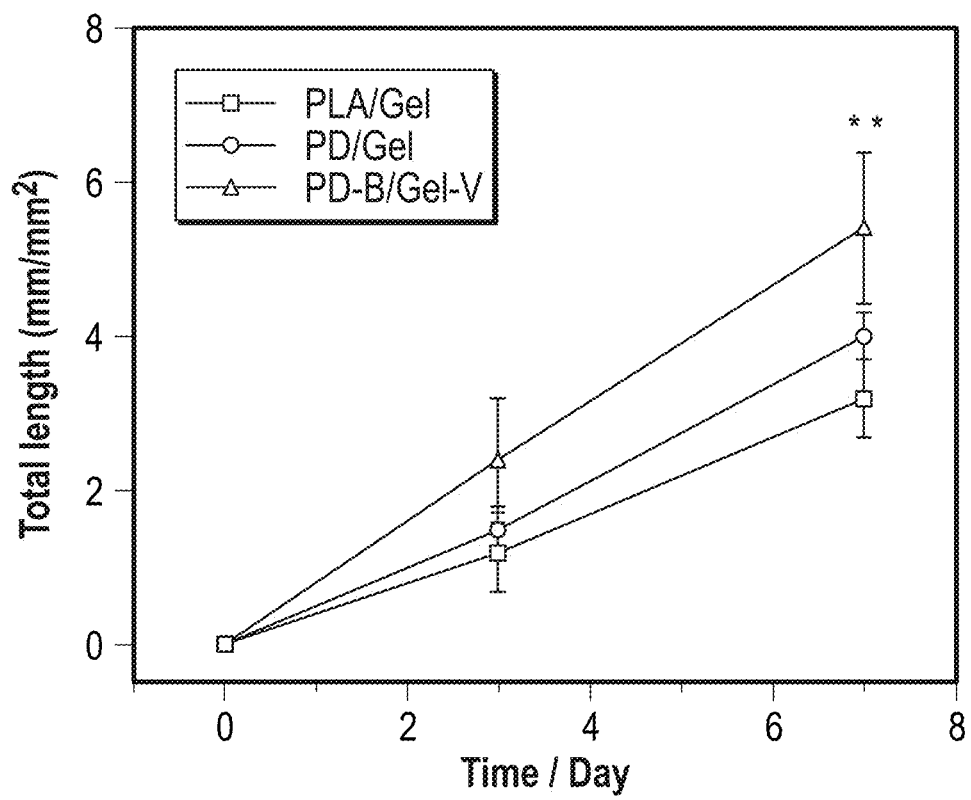
FIG. 16 is a data plot showing quantitative analysis of the extent of capillary-like network formation by measuring total capillary-like length per unit of area, according to an exemplary embodiment of the present disclosure.
Figure 17:
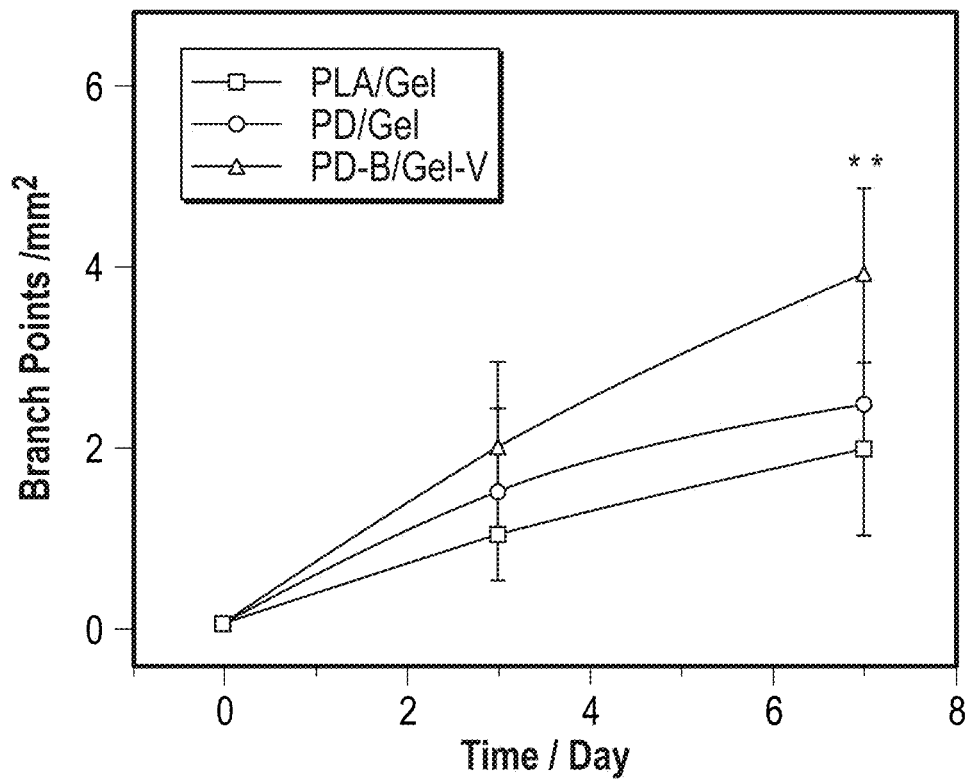
FIG. 17 is a data plot showing quantitative analysis of the extent of capillary-like network formation by measuring the number of branch points per unit of area, according to an exemplary embodiment of the present disclosure.

The successful regeneration of large engineered tissues must include functional blood vessel structures within the implants for oxygen and nutrient transport to maintain skeletal tissue functions. Fluid flow in a bioreactor can be directed through hollow microchannels within the constructs and perfused through the bulk of the hydrogel. This perfusion system can be used to mimic the haemodynamic force and pressure that occur in the natural human body, which can improve the ECM production and mechanical properties of the artificial vessel. In order for vessel functionalization to occur, vessels must mature successively at the level of the endothelium and vessel wall in a networked manner. At the network level, maturation involves remodeling into a hierarchically branched network with adaptation of vascular patterning to local tissue needs. Vascular functionality can be assessed through partial observation of lumen-like vascular channel (cell migration, arrangement and tubular structure) and capillary-like vascular network (diameter, length, inter-capillary distance, branching patterns and tortuosity) morphologies using confocal imaging. After one week of culture, representative fluorescent images showed HUVECs encapsulated in hydrogel were inclined to aggregate and migrate to form annular ring patterns along the channel, as shown in FIG. 14. FIG. 14 also confirms that the vascular lumen wall can be formed originating from endothelial cell layers, and the hollow structure of the artificial vessel may allow native vessel invasion and integration. Thereby the presently disclosed patterned 3D bioprinting with perfused channels is an advantageous technique for creating a large blood vessel in complex constructs. Additionally, it has been reported that hypoxic conditions had a positive effect on controlling capillary formation in vitro by promoting hypoxia-induced VEGF expression, however, it has also been shown to inhibit hMSC differentiation into osteoblasts. Co-culture of hMSCs and HUVECs on scaffolds have often exhibited a negative result on vascularized bone formation in bioreactor relative to static culture. It is difficult to mimic heterogeneous cellular response by modulating oxygen tension via an independent controlled manner in co-culture study. Comparatively, the inner region of 3D bioprinted hydrogels may create a hypoxic environment for the encapsulated HUVECs by a gradient diffusion control of oxygen tension while it has little influence on oxygen supplement for the bone scaffold region. FIG. 15 clearly reveals extensive capillary networks formed within all constructs suggesting that the oxygen gradient may be maintained within the hydrogels. The extent of capillary-like network formation was quantified in the hydrogel region by observing total network length and number of branch points, as shown in FIGS. 16 and 17. Compared to the controls, the PD-B/Gel-V group exhibited a more enhanced capacity for capillary network formation due to the presence of the specific VEGF receptor-binding domain. Therefore, all results indicated that this design potentially provided an efficient approach for artificially fabricating blood vessels composed of a large vessel channel and capillary networks. This would enable the formation of a circulatory, stable vascular network with hierarchical structure, which is a crucial step for regenerating mature vascularized bone.

Figure 18:
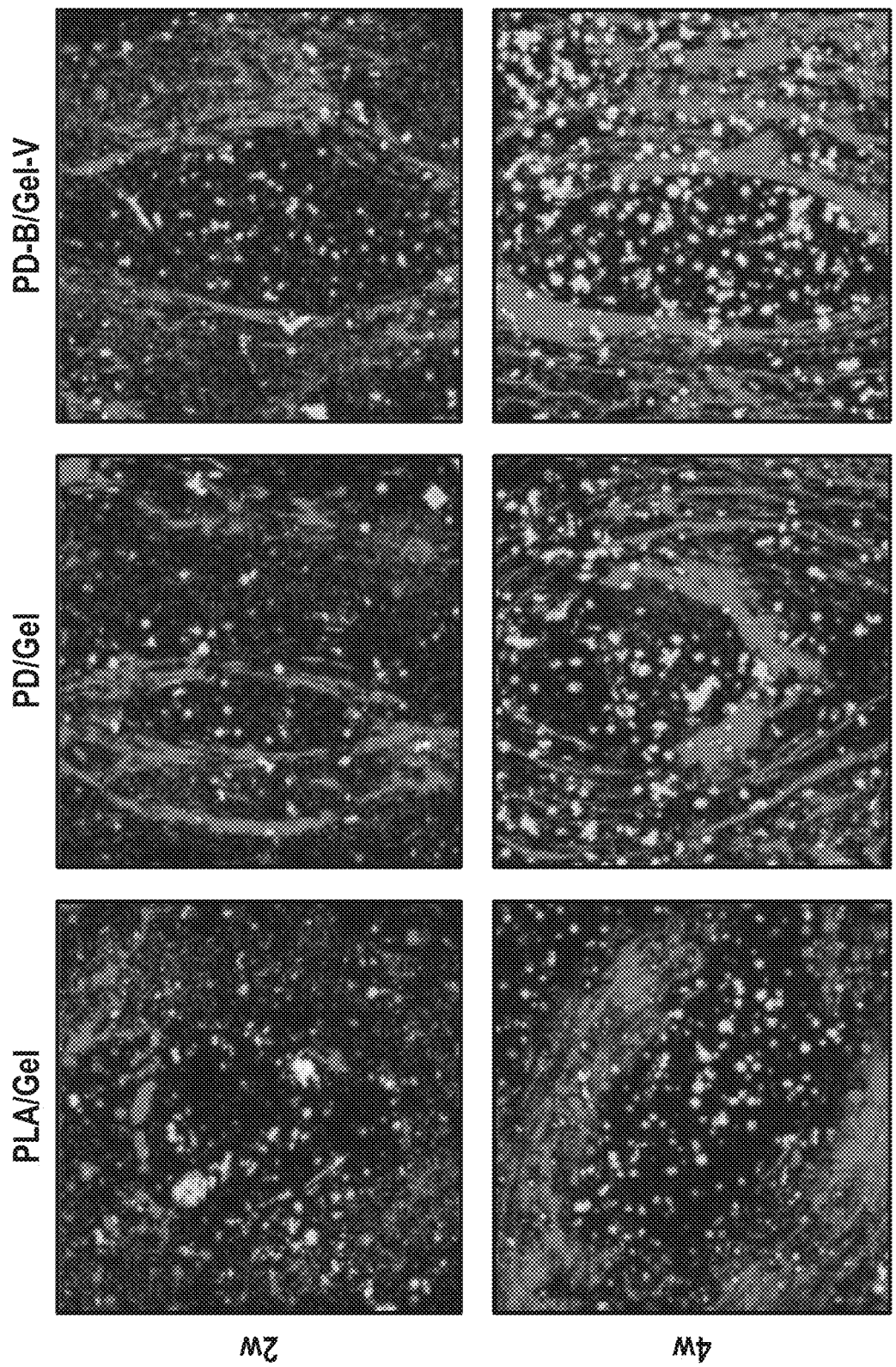
FIG. 18 depicts immunofluorescence images of osteogenesis and angiogenesis (with 100 μm scale bar indicating scale), in particular immunofluorescence staining of the vascularized biphasic tissue construct mimicking bone, according to an exemplary embodiment of the present disclosure.
Figure 19:
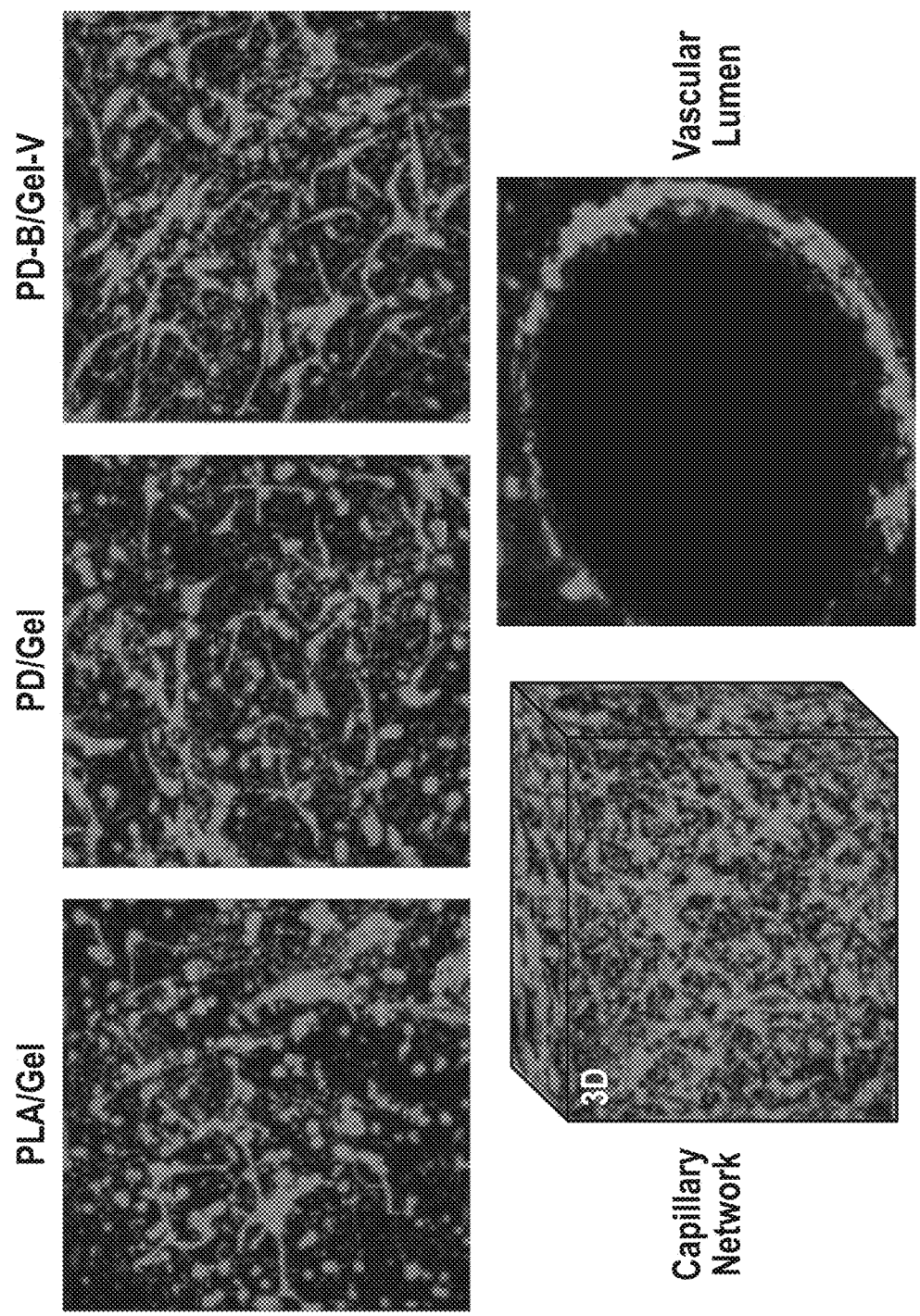
FIG. 19 depicts immunofluorescence images of osteogenesis and angiogenesis (with 50 μm scale bar indicating scale), in particular immunofluorescence staining of the vascular capillary network and lumen identified positive for human CD31 antibody in the targeted regions after 4 weeks, according to an exemplary embodiment of the present disclosure.

The maturation of bone and vascular tissue on the scaffolds after 4 weeks of culture was further assessed using immunofluorescence staining of the osteogenic differentiation marker osteopontin (OPN, red) and angiogenic specific marker von Willebrand factor (vWf, green), respectively. All of the cell differentiation experiments were implemented in the bioreactor with static culture as the control. As shown in FIG. 18, the marked red staining on PD-B/Gel-V constructs illustrated a higher osteogenic ability, supporting that this BMP2 peptide fragment as growth factor analogs can promote the activation of the Smad pathway through binding receptors to further improve osteogenesis. Moreover, the VEGF peptide group also displayed more significant angiogenesis. The fluorescence images for anti-von Willebrand factor (vWF, green) and osteopontin (OPN, red) showed that the PD-B/Gel-V construct possessed higher angiogenesis and osteogenesis than other control groups. In addition, CD31, which is a typical marker of endothelial cells, was stained to further verify capillary network formation. FIG. 19 indicates that the 3D bioprinted hydrogel region offered a permissive environment for capillary network formation in vitro, and the VEGF peptide immobilization promoted angiogenic differentiation. As mentioned above, the GelMA hydrogel may provide an expansionary space for inner capillary network development due to the gradual degradation of MMP-sensitive fragment by HUVECs therein. The images presented a proof-of-concept design in which large vessels branched out internally into smaller capillary units throughout the scaffolds in a random, circular or longitudinal pattern.

Figure 20A:
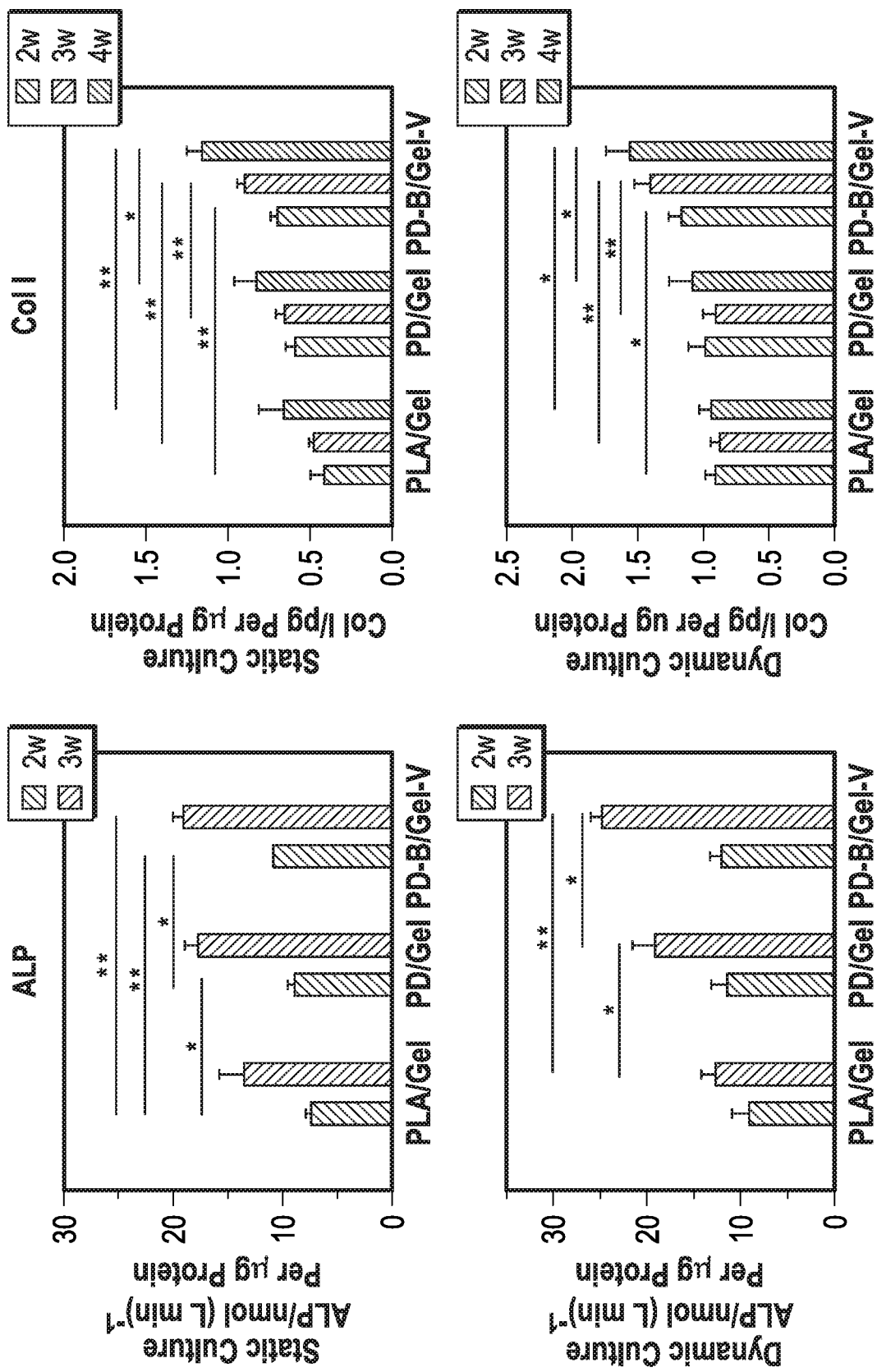
FIG. 20A and FIG. 20B depict data plots showing quantification of ALP activities, collagen type I (Col I) synthesis, VEGF expression, and calcium deposition on different biphasic tissue constructs showing that the PD-B/Gel-V construct enhanced the osteogenic and angiogenic differentiation, according to an exemplary embodiment of the present disclosure.
Figure 20B:
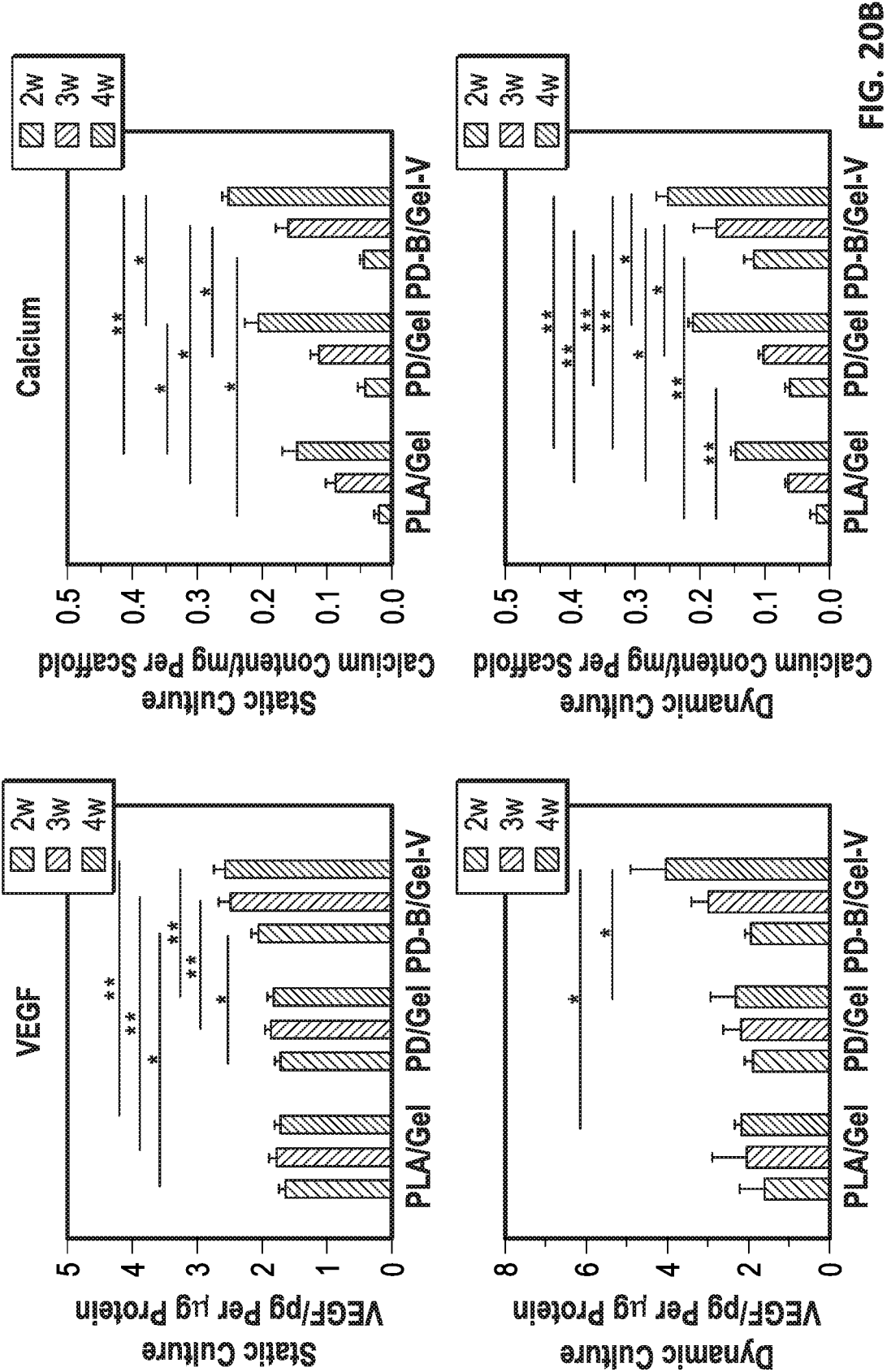

Furthermore, osteogenic and angiogenic differentiation in the presently disclosed constructs was evaluated quantitatively by measuring alkaline phosphatase (ALP) activity, determining collagen type I (Col I) expression, assaying VEGF secretion, and quantifying calcium deposition, as shown in FIGS. 20A and 20B. The PD-B/Gel-V group showed a higher expression in the ALP activity after 2 weeks of induction, both in static and dynamic culture conditions, when compared to other groups. As an early protein of osteogenesis, ALP activity data suggested BMP2 immobilization could enhance the hMSCs differentiation toward osteoblasts. Moreover, ALP activity of hMSCs in bioreactor culture exhibited a more rapid increase relative to static culture. Col I is a main component for bone ECM, its synthesis in cells was measured to investigate the ability of the presently disclosed constructs to facilitate osteogenic differentiation. Compared with the control groups, hMSCs on PD-B/Gel-V constructs expressed significantly higher Col I. In addition, the Col I content of hMSCs in the bioreactor system was much higher than those in the static condition. VEGF secretion is an important signaling protein which is involved in angiogenesis. Results showed a significant increase of VEGF level in the PD-B/Gel-V group over the whole study period, suggesting that immobilized VEGF peptides could enhance signaling and bioactivity of endothelial cells and thus angiogenesis, in vitro. Remarkably, the VEGF expression in the dynamic culture is up to 30% higher than that in static culture after 4 weeks. As described above, incubation of constructs in the bioreactor system produced enhanced angiogenesis by mimicking the haemodynamic forces and providing a hypoxic environment through gradient oxygen diffusion. Mineralization or calcium deposition is the most critical indicator of osteogenic differentiation. Thus, the calcium deposition content on all scaffolds was investigated after 4 weeks of culture. These results also confirmed that the PD-B/Gel-V constructs showed increased calcium deposition, attributing to enhanced osteoinduction by BMP2 peptides and the charged surface of peptides as nucleation sites for mineralization. In addition, dynamic culture presented improved calcium deposition, indicating mechanical cues by shear stress could be beneficial to osteogenic differentiation and mineralization.

Perfusion culture in the bioreactor resulted in more uniform nutrient transport and well-timed gas exchange relative to static culture. It was determined that for the presently disclosed biphasic constructs, dual bioactive factors with regional distribution further provides a targeted stimulus for osteogenesis and angiogenesis in respective sites. Moreover, immobilized peptides keeps prolonged retention and bioavailability for sustained fostering of target tissue, avoiding repetitive protein deliveries and additional treatments, and reducing cost. Overall, all results demonstrated that the presently disclosed dual 3D bioprinted constructs integrating a biomimetic bone-like structure with regional bioactive peptides exhibited an outstanding therapeutic efficacy for vascularized bone regeneration that may be utilized in a clinical setting.

EXAMPLES

Design and Fabrication of Hierarchical Construct

In order to mimic native bone, "honeycombed pore shaped" scaffold units were prepared using a FDM 3D printer. The prepared constructs were composed of stacked units with a 200 μm line distance and a 200 μm layer height to form a porous cylinder, which is similar to the cylindrical structures of osteon or haversian systems. In addition, a series of interconnected horizontal and vertical vascular channels were designed to provide a biomimetic fluid environment for in vitro study and invasion spaces of native blood vessels for in vivo implantation. A 2 mm marrow, cavity-like vascular channel was located in the center of the construct and some 500 μm diameter vascular channels pass through the entire bone region of the scaffold allowing the culture medium unobstructed infusion.

The scaffold was fabricated as a biphasic scaffold through dual bioprinting manufacturing technology in a two-step manner. First, a table-top FDM 3D bioprinter and a SLA based 3D bioprinter were developed based on the existing rapid prototyping platforms for use as a proof-of-concept 3D bioprinting system for advanced manufacturing of hierarchical constructs. The hard bone regions in the construct were fabricated first using PLA on the FDM bioprinter. Subsequently, the SLA bioprinter (laser beam ~190 μm; wavelength ~355 nm; intensity output of emitted UV ~20 μJ at 15 kHz) was used to print the elastic vascular structure by infilling the interconnected channels and pores with cell-laden GelMA hydrogel in the remaining space of the constructs. In order to obtain a cylindrical channel in the hydrogels, a needle-based subtractive technique was performed to extract a lumen structure in the cell-laden hydrogel using a stainless steel microneedle. GelMA was synthesized as photocurable bioink for SLA bioprinting. Methacrylic anhydride (MA) (1% (v/v), Sigma-Aldrich) was added dropwise to the gelatin (Sigma-Aldrich, 10% in PBS (w/w)) solution while stirring, and then the mixture was reacted for 3 h at 50° C. The GelMA solution was dialyzed against deionized water for 7 d at 50° C. The dialyzed GelMA solutions were lyophilized, and stored at room temperature. Before use, a GelMA polymer solution was prepared by dissolving the freeze-dried GelMA and the photoinitiator (Irgacure 2959) (0.5 w/v %) in PBS (0.01 M). Finally, representative CAD models and Slic3r configuration of the hierarchical construction were used to analyze and calculate all structural parameters, including the wall thickness, pore size, porosity, and channel size. A representative construct was determined to have a wall thickness of the PLA scaffold (~250 μm), pore size (~250 μm), porosity (~20%), small channel size of construct (~200 μm) and central channel size of construct (~1.5 mm).

Regional Fabrication of Bioactive Factors

During the 3D scaffold printing process, the osteogenic and angiogenic peptides were immobilized onto corresponding regions, respectively. The peptide sequence, KIPKASSVPTELSAISTLYLNH2, represents a specific domain of BMP2. A cysteine amino acid at the N-terminus of this sequence was designed and introduced to allow its further reaction with the other active group. Through the same method, another peptide with a thiol group at the N terminus was also designed and prepared to mimic VEGF protein with the peptide sequence, KLTWQELYQLKYKGINH2. Peptides were obtained with more than 95% purity according to the HPLC profile provided by the manufacturer (GenScript). BMP2 peptide was bonded on the PLA scaffold's surface by mussel-inspired chemistry. PLA scaffolds were immersed in a dopamine (DA) solution (2 mg/mL in 10 mM Tris-HCl, pH 8) and placed on a shaker for 12 h in the presence of oxygen at room temperature. After 12 h, they were rinsed with distilled water five times, and then the polydopamine (pDA)-coated scaffolds were immersed in 20 ng/mL BMP2 peptide solution. Finally, the scaffolds were washed with distilled water three times to remove the unattached peptides. Correspondingly, VEGF peptide (50 ng/mL) was conjugated into the hydrogel via click chemistry during SLA bioprinting. ATR-FTIR spectroscopy measurements were performed with a Perkin Elmer Spectrum BX system, to detect changes of all component structures in the engineered scaffolds construction.

Mechanical and Morphological Characterization of Constructs

The mechanical properties of all scaffolds were tested using a MTS criterion universal testing system equipped with a 100 N and 50 k N load cell (MTS Corporation, US), according to International Organization for Standardization (ISO) and American Society for Testing and Materials (ASTM). The scaffolds were compressed at a strain rate of 2 mm/min to a maximum strain of 20%. The slope of the linear elastic region of the stress-strain curve was calculated to obtain the compressive modulus. The morphology and surface topography of constructs for both the PLA scaffold and the GelMA gel segments were studied using a Zeiss SigmaVP scanning electron microscope (SEM). All scaffolds were coated with a 10 nm thick gold layer and imaged using 5 kV electron beam.

hMSCs and HUVECs Culture Protocol hMSCs (Texas A&M Health Science Center, Institute for Regenerative) were cultured in mesenchymal stem cell growth medium (MSCGM) consisting of alpha minimum essential medium, 20% fetal bovine serum (FBS), 1% L-glutamine, and 1% penicillin/streptomycin. HUVECs (Life Technologies) were cultured in endothelial growth medium (EGM) consisting of Medium 200 and low serum growth supplement (LSGS). For osteogenic differentiation studies, hMSCs were cultured in osteoinductive medium (OM, MSCGM supplemented with 10 nM dexamethasone, 50 μg/mL L-ascorbate acid and 10 mM β-glycerophosphate (Sigma)). All experiments were performed with hMSCs and HUVECs of six cell passages or less.

Cell Adhesion, Encapsulation and Proliferation

In order to study the effect of pDA and BMP2 peptides on hMSC attachment, the cells ($2\times10^5$ cells/mL) were seeded on various scaffolds for 4 h. The samples were assessed by the 3-(4,5-dimethylthiazol-2-yl)-2,5-diphenyltetrazolium bromide (MTT) assay. MTT solution (0.5 mg/mL) was added in the plate and then incubated for 4 h. After the medium was removed, isopropanol/HCl solution (1 M) was added to dissolve the formazan crystals. The optical density (OD) was measured at 490 nm by photometric plate reader (Thermo Scientific). The cell proliferation on these scaffolds was conducted for 1, 3 and 5 days. Samples were seeded with $1\times10^5$ cells/mL and counted at each time point using the same MTT assay described above. HUVECs and hMSCs ($1\times10^6$ cells/mL) were respectively mixed with sterile GelMA solution, and then added to SLA bioprinting platform. After bioprinting via photocuring, a qualitative viability assay was performed using a live-dead assay kit for 1, 3 and 7 days of culture. At the predesigned day, post-encapsulation, the cell/hydrogel complexes were treated with calcein AM (2 μM) and propidium iodide (4 μM). Samples were observed and imaged using a Zeiss 710 confocal microscope. The HUVEC proliferation was measured to investigate cell activity when cells ($1\times10^6$ cells/mL) were encapsulated in hydrogel. After the predetermined period, the incubation medium was changed with alamar blue assay solution (10% v/v in medium) (Invitrogen). After 4 h of incubation, the absorbance values of supernatant solution were measured at 570 and 600 nm on photometric plate reader.

Construction of Vascularized Bone Grafts

For visualized vascularized bone grafts, the fluorescent labeled cell study was conducted on the aforementioned 3D scaffolds. Before cell seeding, hMSCs and HUVECs were incubated with CMFDA and CMTMR (10 μM Molecular Probes, CellTracker™ Dye, life technologies) for 30 min each at 37° C., respectively. hMSCs, stained with red dye ($2\times105$ cells/mL), were seeded first onto hard scaffolds for 24 h to ensure cell adhesion. According to the previous study, a 1:1 ratio was optimally chosen in co-culture studies as it provided robust and stable vascular networks. hMSCs (red) and HUVECs (green) ($1\times10^6$ cells/mL) were mixed in GelMA solution with a 1:1 ratio and then photocured to form cell-laden hydrogels by SLA bioprinting. The cell location or arrangement in the 3D bioprinted vascularized bone constructs was imaged with confocal microscope. To investigate the effect of the scaffold's surface features on the hMSC spreading and hydrogel encapsulation for HUVEC phenotype, the organization of actin filaments was evaluated after cells were cultured on our constructs for 3 d. The cells' cytoskeleton was identified with double staining of actin (red) using Texas Red labeled phalloidin and nuclei (blue) using 4,6-diamidino-2-phenylindole dihydrochloride (DAPI) (Invitrogen). Cells were fixed in 10% formalin for 15 min, permeabilized in 0.1% Triton X-100, and blocked with 1% BSA. Cells were then incubated with phalloidin for 20 min and DAPI for 3 min. Samples were observed and imaged using confocal microscope.

Dynamic Culture in Bioreactor

In order to mimic surrounding fluid present in vivo, a custom-designed flow bioreactor system was utilized for incubating cells on 3D bioprinted constructs to study vascularized bone formation in dynamic culture. The culture medium was perfused through constructs using a digital peristaltic pump (Masterflex, Cole-Parmer) at a flow rate of 5 mL/min over the whole experiment period. A fluid reservoir provided the culture medium for circulation and a port for gas exchange with 5% CO2/95% air. Efficient transfer of nutrients and oxygen is facilitated by the convective forces provided by creep flow as the medium flows through the cell/scaffold constructs. Static culture served as the control and was identically operated in the tissue culture wells. To perform this dynamic development in our constructs, representative hydrodynamic parameters specifically permeability (KD) were calculated using Darcy's Law:

$$K_D = \frac{\mu Q L}{A \Delta P},\qquad\text{Eqn. 1}$$

where μ is the viscosity of the perfusing fluid (culture medium, $8\times10^{-4}$ Pa·s at 37° C.), Q is volumetric flow rate (cm³/s), L is the thickness of the sample (cm), A is the cross-sectional area (cm²), and ΔP is the pressure gradient (230±65 Pa in hydrogel region for our constructs). The average shear stress (τ) applied over the cell surface cultured in constructs was calculated by the modified Brinkman equation:

$$\tau = \frac{B\mu Q}{A\sqrt{K_D}}\qquad\text{Eqn. 2}$$

where τ is the average shear stress over the cell surface (dyn/cm2), and B is the Brinkman constant for flow around cells (B=3/π for spheres).

In Vitro Capillary-Like Networks and Vascular Lumen-Like Channel Formation

In order to investigate the capability of vascular formation in the soft segment of the constructs for 1 w, GelMA hydrogels with hMSCs and HUVECs were printed by an SLA bioprinter. HUVECs were stained with CMTMR and hMSCs were co-encapsulated into the hydrogel using the same culture and staining protocol described above. After 3 and 6 days of culture, capillary-like networks and lumen-like channels were visualized by red fluorescence using the confocal microscope. The total capillary-like length and the number of capillary-like branch points were quantified on 3D projected confocal images.

Vascularized Bone Formation

In order to induce vascularized bone formation, the vascularized bone grafts, co-cultured with hMSCs and HUVECs using the same protocol described above, were divided into two culture condition groups in the bioreactor: static co-culture and dynamic co-culture. The optimal culture condition is to utilize EGM for 1 week and then a mixed medium composed by EGM and OM at 1:1 ratio for 3 weeks. At predesigned time points, cells were digested in lysed buffer via ultrasonic method and freeze-melt method. The lysate was collected by centrifuge to test alkaline phosphatase (ALP) activity, collagen type I (Col I) and VEGF secretion. The ALP activity was determined for 7 and 14 days using ALP assay kit (Bioassay Systems) after the initiation of hMSC osteogenic differentiation. ALP substrate was added to the digested suspension in the dark for 30 min, and then the absorbance was read at 405 nm. Measurements were compared to p-nitrophenol standards and normalized to total cell protein. The Col I and VEGF were determined by Col I ELISA Kit (TSZ ELISA) and VEGF ELISA Kit (Thermo Fisher Scientific) according to the manufacturer's instructions, respectively. In order to assay calcium deposition or mineralization nodules on the scaffolds, a calcium detection kit (Pointe Scientific) was used to quantify the calcium deposition. The calcium deposition on scaffolds was dissolved in 0.6 M HCl, and reacted with dye reagent. Samples were read at 570 nm wavelength, and the contents were calculated with $CaCl_2$ standards. For immunostaining of capillary-like network, cell-laden hydrogel segments were fixed in 10% formalin for 15 min, and permeabilized with Triton X-100 (0.1%) in PBS for 15 min. The hydrogels were then blocked with bovine serum albumin (BSA) for 1 h, followed by overnight incubation with primary antibodies (Anti-CD31 antibody, abcam). The hydrogels were incubated with chicken anti-mouse IgG-TR secondary antibodies (Santa Cruz Biotechnology) overnight. Finally, the hydrogels were stained with DAPI, and imaged using a confocal microscope. For immunofluorescence staining of vascularized bone, the cells were fixed with 10% formalin for 15 min, permeabilized in 0.1% Triton X-100 for 15 min and blocked in 10% BSA for 30 min. Then the cells were incubated with primary antibodies at 4° C. overnight. The following primary antibodies were used for staining: goat polyclonal anti-von Willebrand factor (vWF) antibodies (Santa Cruz Biotechnology) and mouse monoclonal anti-osteopontin (OPN) antibodies (Santa Cruz Biotechnology). After incubation with primary antibodies, donkey anti-goat IgG-FITC (Santa Cruz Biotechnology) and chicken anti-mouse IgG-TR as secondary antibodies were added and incubated 1 h, respectively. Fluorescence images were observed using a confocal microscope.

Statistical Analysis

The data are presented as the mean±SD (standard deviation). A one-way analysis of variance (ANOVA) with Student's t-test was used to verify statistically significant differences among groups, with $p<0.05$ being statistically significant (*, $p<0.05$; , $p<0.01$; *, $p<0.001$).

Statements of the Disclosure Include:

Statement 1: A biphasic tissue construct comprising: a scaffold having one or more channels; and a vascular portion comprising a hydrogel, the vascular portion at least partially disposed in the one or more channels.

Statement 2: A biphasic tissue construct according to Statement 1, further comprising a first bioactive growth factor and a second bioactive growth factor different from the first bioactive growth factor, the first bioactive growth factor localized to the scaffold and the second bioactive growth factor localized to the vascular portion.

Statement 3: A biphasic tissue construct according to Statement 2, wherein the first bioactive growth factor is bone morphogenetic protein 2 (BMP2) peptide and the second bioactive growth factor is vascular endothelial growth factor (VEGF) peptide.

Statement 4: A biphasic tissue construct according to Statement 3, further comprising bone morphogenetic protein 2 (BMP2) peptides immobilized on a surface of the scaffold.

Statement 5: A biphasic tissue construct according to Statement 3, wherein a surface of the scaffold forming a wall of the one or more channels comprises one or more immobilized BMP2 peptides.

Statement 6: A biphasic tissue construct according to Statement 4 or Statement 5, wherein the BMP2 peptides are immobilized using biocompatible mussel-inspired chemistry.

Statement 7: A biphasic tissue construct according to any one of the preceding Statements 1-6, wherein the scaffold comprises a material that is degradable in the human body.

Statement 8: A biphasic tissue construct according to any one of the preceding Statements 1-7, wherein the scaffold comprises a material selected from the group consisting of biodegradable polylactic acid (PLA) fibers, polycaprolactone (PCL), poly(lactic-co-glycolic acid) (PLGA), and any combination thereof.

Statement 9: A biphasic tissue construct according to any one of the preceding Statements 1-8, wherein the scaffold is coated with polydopamine (pDA).

Statement 10: A biphasic tissue construct according to any one of the preceding Statements 1-9, wherein the scaffold comprises a material having a compression modulus from about 0.03 to about 0.6 GPa.

Statement 11: A biphasic tissue construct according to any one of the preceding Statements 1-10, wherein the scaffold is seeded with human mesenchymal stem cells (hMSCs).

Statement 12: A biphasic tissue construct according to any one of the preceding Statements 1-11, wherein a surface of the scaffold forming a wall of the one or more channels further comprises one or more human mesenchymal stem cells (hMSCs).

Statement 13: A biphasic tissue construct according to Statement 9, further comprising BMP2 peptides immobilized on a surface of pDA coating.

Statement 14: A biphasic tissue construct according to any one of the preceding Statements 1-13, wherein the scaffold is fabricated using a fused deposition modeling (FDM) 3D bioprinter.

Statement 15: A biphasic tissue construct according to any one of the preceding Statements 1-14, wherein the scaffold comprises at least one channel having a diameter from about 500 μm to about 2000 μm and at least one channel having a diameter from about 20 μm to about 200 μm.

Statement 16: A biphasic tissue construct according to any one of the preceding Statements 1-15, wherein the scaffold comprises one or more central channels and a plurality of peripheral channels, the one or more central channels having a diameter from about 500 µm to about 2000 µm and the plurality of peripheral channels having a diameter from about 20 µm to about 200 µm.

Statement 17: A biphasic tissue construct according to any one of the preceding Statements 1-16, wherein the hydrogel is a gelatin methacrylate (GelMA) hydrogel.

Statement 18: A biphasic tissue construct according to any one of the preceding Statements 1-17, wherein the hydrogel further comprises one or more human mesenchymal stem cells (hMSCs) and one or more human umbilical vein endothelial cells (HUVECs).

Statement 19: A biphasic tissue construct according to any one of the preceding Statements 1-18, wherein the vascular portion is fabricated using a stereolithography (SLA) 3D bioprinter.

Statement 20: A biphasic tissue construct according to any one of the preceding Statements 1-20, prepared using a hydrogel polymer solution concentration of from about 5 wt % to about 30 wt %.

Statement 21: A biphasic tissue construct according to any one of the preceding Statements 1-20, wherein the hydrogel comprises vascular endothelial growth factor (VEGF) peptides.

Statement 22: A biphasic tissue construct according to Statement 21, wherein the hydrogel is covalently conjugated to the VEGF peptides using a thiol-ene click reaction.

Statement 23: A biphasic tissue construct according to any one of the preceding Statements 1-22, wherein the hydrogel comprises a lumen structure.

Statement 24: A biphasic tissue construct according to according to any one of the preceding Statements 1-23 for implantation in a patient in need of tissue replacement or tissue regeneration therapy.

Statement 25: A biphasic tissue construct according to according to any one of the preceding Statements 1-23 for implantation in a patient in need of bone replacement or bone regeneration therapy.

Statement 26: A method of treating a patient in need of tissue replacement or tissue regeneration, the method comprising implanting the biphasic tissue construct according to any one of the preceding Statements 1-23 into the patient.

Statement 27: A method of treating a patient in need of bone replacement or bone regeneration, the method comprising implanting the biphasic tissue construct according to any one of the preceding Statements 1-23 into the patient.

Statement 28: A system comprising the biphasic tissue construct according to any one of the preceding Statements 1-23 and a bioreactor configured to promote vascularization and osteogenesis in the biphasic tissue construct.

Statement 29: A method of fabricating a biphasic tissue construct, the method comprising: generating a scaffold having one or more channels; depositing a first bioactive growth factor on a surface of the scaffold; seeding the scaffold with human mesenchymal stem cells (hMSCs); forming a vascular portion at least partially disposed in the one or more channels to form a biphasic construct, wherein the vascular portion comprises: a hydrogel; a second bioactive growth factor; and one or more selected from the group consisting of human mesenchymal stem cells (hMSCs) and human umbilical vein endothelial cells (HUVECs).

Statement 30: A method of fabricating a biphasic tissue construct according to Statement 29, wherein the first bioactive growth factor is bone morphogenetic protein 2 (BMP2) peptide and the second bioactive growth factor is vascular endothelial growth factor (VEGF) peptide.

Statement 31: A method of fabricating a biphasic tissue construct according to Statement 29 or Statement 30, wherein the scaffold comprises biodegradable polylactic acid (PLA) fibers and the hydrogel is a gelatin methacrylate (GelMA) hydrogel.

Statement 32: A method of fabricating a biphasic tissue construct according to Statement 30 or Statement 31, further comprising immobilizing the bone morphogenetic protein 2 (BMP2) peptide on a surface of the scaffold using biocompatible mussel-inspired chemistry and causing the vascular endothelial growth factor (VEGF) peptides to be covalently conjugated to the hydrogel using a thiol-ene click reaction.

Statement 33: A method of fabricating a biphasic tissue construct according to any one of the preceding Statements 29-32, further comprising coating the surface of the scaffold with polydopamine (pDA).

Statement 34: A method of fabricating a biphasic tissue construct according to any one of the preceding Statements 29-33, forming a lumen structure in the vascular portion using a subtractive needle technique Statement 35: A method of fabricating a biphasic tissue construct according to any one of the preceding Statements 29-34, further comprising incubating the biphasic construct in a bioreactor to promote vascularization and osteogenesis.

Statement 36: A method of fabricating a biphasic tissue construct according to any one of the preceding Statement 29-35, wherein the scaffold is generated using a fused deposition modeling (FDM) 3D bioprinter and the vascular portion is formed using a stereolithography (SLA) 3D bioprinter.

Statement 37: A method of fabricating a biphasic tissue construct, the method comprising: generating a scaffold having one or more channels; forming a vascular portion at least partially disposed in the one or more channels to form a biphasic construct, the vascular portion comprising a hydrogel; and depositing a first bioactive growth factor and a second bioactive growth factor different from the first bioactive growth factor on the biphasic tissue construct such that the first bioactive growth factor is substantially localized to the scaffold and the second bioactive growth factor is substantially localized to the vascular portion.

Statement 38: A method of fabricating a biphasic tissue construct according to Statement 37, wherein the first bioactive growth factor is bone morphogenetic protein 2 (BMP2) peptide and the second bioactive growth factor is vascular endothelial growth factor (VEGF) peptide.

Statement 39: A method of fabricating a biphasic tissue construct according to Statement 37 or Statement 38, wherein the scaffold comprises biodegradable polylactic acid (PLA) fibers and the hydrogel is a gelatin methacrylate (GelMA) hydrogel.

Statement 40: A method of fabricating a biphasic tissue construct according to Statement 38 or Statement 39, further comprising immobilizing the bone morphogenetic protein 2 (BMP2) peptide on a surface of the scaffold using biocompatible mussel-inspired chemistry and causing the vascular endothelial growth factor (VEGF) peptides to be covalently conjugated to the hydrogel using a thiol-ene click reaction.

Statement 41: A method of fabricating a biphasic tissue construct according to any one of the preceding Statements 37-40, further comprising coating the surface of the scaffold with polydopamine (pDA).

Statement 42: A method of fabricating a biphasic tissue construct according to any one of the preceding Statements 37-41, forming a lumen structure in the vascular portion using a subtractive needle technique Statement 43: A method of fabricating a biphasic tissue construct according to any one of the preceding Statements 37-42, further comprising incubating the biphasic construct in a bioreactor to promote vascularization and osteogenesis.

Statement 44: A method of fabricating a biphasic tissue construct according to any one of the preceding Statement 37-43, wherein the scaffold is generated using a fused deposition modeling (FDM) 3D bioprinter and the vascular portion is formed using a stereolithography (SLA) 3D bioprinter.

Statement 45: A method of fabricating a biphasic tissue construct according to any one of the preceding Statements 29-44, wherein the scaffold comprises biodegradable polylactic acid (PLA) fibers, polycaprolactone (PCL), poly(lactic-co-glycolic acid) (PLGA), and any combination thereof.

Statement 46: A method of fabricating a biphasic tissue construct according to any one of the preceding Statements 29-44, wherein a hydrogel polymer solution concentration of from about 5 wt % to about 30 wt % is used to form the vascular portion of the biphasic tissue construct.

Statement 47: A system comprising: a biphasic tissue construct comprising: a scaffold having one or more channels and seeded with one or more human mesenchymal stem cells (hMSCs); a first bioactive growth factor immobilized on a surface of the scaffold; and a vascular portion at least partially disposed in the one or more channels, the vascular portion comprising: a hydrogel; a second bioactive growth factor different from the first bioactive growth factor; and one or more selected from the group consisting of human mesenchymal stem cells (hMSCs) and human umbilical vein endothelial cells (HUVECs); and a bioreactor configured to promote vascularization and osteogenesis in the biphasic tissue construct.

We claim:

1. A biphasic tissue construct that prior to in vivo implantation comprises:
    a hard scaffold having one or more channels, wherein the hard scaffold is comprised of a hard material having a high mechanical strength that mimics the mineralized component of native bone;
    a vascular portion comprising a hydrogel, wherein the hydrogel is deposited into one or more channels of the hard scaffold such that the vascular portion is at least partially disposed in the one or more channels, wherein the hydrogel forms a cylindrical channel comprising a lumen structure; and
    a first bioactive growth factor and a second bioactive growth factor different from the first bioactive growth factor, the first bioactive growth factor localized to the hard scaffold and the second bioactive growth factor localized to the vascular portion.

2. The biphasic tissue construct according to claim 1, wherein the first bioactive growth factor is bone morphogenetic protein 2 (BMP2) peptide and the second bioactive growth factor is vascular endothelial growth factor (VEGF) peptide.

3. The biphasic tissue construct according to claim 2, wherein the bone morphogenetic protein 2 (BMP2) peptide is immobilized on a surface of the scaffold.

4. The biphasic tissue construct according to claim 1, wherein the scaffold comprises biodegradable polylactic acid (PLA) fibers, polycaprolactone (PCL), poly(lactic-co-glycolic acid) (PLGA), or any combination thereof.

5. The biphasic tissue construct according to claim 4, wherein the scaffold is coated with polydopamine (pDA).

6. The biphasic tissue construct according to claim 1, wherein the hard scaffold comprises a hard material having a compression modulus from 0.03 to 0.6 GPa.

7. The biphasic tissue construct according to claim 1, wherein the one or more channels comprises at least one channel having a diameter from 500 μm to 2000 μm and at least one channel having a diameter from 20 μm to 200 μm.

8. The biphasic tissue construct according to claim 1, wherein the scaffold comprises one or more central channels and a plurality of peripheral channels, the one or more central channels having a diameter from 500 μm to 2000 μm and the plurality of peripheral channels having a diameter from 20 μm to 200 μm.

9. The biphasic tissue construct according to claim 1, wherein the hydrogel is a gelatin methacrylate (GelMA) hydrogel.

10. The biphasic tissue construct according to claim 9, wherein the hydrogel comprises vascular endothelial growth factor (VEGF) peptides covalently conjugated to the hydrogel using a thiol-ene click reaction.

11. The biphasic tissue construct according to claim 1, wherein the scaffold is seeded with human mesenchymal stem cells (hMSCs) and the hydrogel is a cell-laden hydrogel comprising one or more selected from the group consisting of human mesenchymal stem cells (hMSCs) and human umbilical vein endothelial cells (HUVECs).

12. The biphasic tissue construct according to claim 1, wherein the vascular portion is prepared using a hydrogel polymer solution concentration of from 5 wt % to 30 wt %.

13. The biphasic tissue construct according to claim 1, wherein the vascular portion comprises a lumen structure.

14. The biphasic tissue construct according to claim 1, wherein the scaffold comprises biodegradable polylactic acid (PLA) fibers and the hydrogel is a gelatin methacrylate (GelMA) hydrogel.

15. The biphasic tissue construct according to claim 1, wherein the scaffold comprises a porosity of between 10% to 40%.

16. A biphasic tissue construct that prior to in vivo implantation comprises:
    a hard scaffold having one or more channels, wherein the hard scaffold is comprised of a hard material having a high mechanical strength that mimics the mineralized component of native bone;
    a vascular portion comprising a hydrogel, wherein the hydrogel is deposited into one or more channels of the hard scaffold such that the vascular portion is at least partially disposed in the one or more channels; and
    a first bioactive growth factor and a second bioactive growth factor different from the first bioactive growth factor, the first bioactive growth factor localized to the hard scaffold and the second bioactive growth factor localized to the vascular portion, wherein the scaffold comprises a plurality of fused stacked units, wherein each unit comprises a honeycombed pore shape so as to produce channels that mimic the osteon or haversian system in native bone.

17. A biphasic tissue construct that prior to in vivo implantation comprises:
    a hard scaffold having one or more channels, wherein the hard scaffold is comprised of a hard material having a high mechanical strength that mimics the mineralized component of native bone;
    a vascular portion comprising a hydrogel, wherein the hydrogel is deposited into one or more channels of the hard scaffold such that the vascular portion is at least partially disposed in the one or more channels, wherein the scaffold is seeded with human mesenchymal stem cells (hMSCs) and the hydrogel is a cell-laden hydrogel comprising one or more selected from the group consisting of human mesenchymal stem cells (hMSCs) and human umbilical vein endothelial cells (HUVECs), wherein the cell-laden hydrogel comprises a lumen structure; and a first bioactive growth factor and a second bioactive growth factor different from the first bioactive growth factor, the first bioactive growth factor localized to the hard scaffold and the second bioactive growth factor localized to the vascular portion.

\* \* \* \* \*